(12) United States Patent
Albert et al.

(10) Patent No.: US 9,770,268 B2
(45) Date of Patent: Sep. 26, 2017

(54) TETHER CLAMP AND IMPLANTATION SYSTEM

(71) Applicants: Michael Albert, Dayton, OH (US); Randy Roof, Matthews, NC (US); Stuart Lindquist, Charlotte, NC (US); John M Kapitan, Asheville, NC (US)

(72) Inventors: Michael Albert, Dayton, OH (US); Randy Roof, Matthews, NC (US); Stuart Lindquist, Charlotte, NC (US); John M Kapitan, Asheville, NC (US)

(73) Assignee: BAND-LOK, LLC, Matthews, NC (US)

( * ) Notice: Subject to any disclaimer, the term of this patent is extended or adjusted under 35 U.S.C. 154(b) by 0 days.

(21) Appl. No.: 15/058,582

(22) Filed: Mar. 2, 2016

(65) Prior Publication Data
US 2016/0175014 A1    Jun. 23, 2016

Related U.S. Application Data

(60) Division of application No. 14/746,226, filed on Jun. 22, 2015, which is a continuation of application No. 13/618,724, filed on Sep. 14, 2012, now Pat. No. 9,173,685.

(60) Provisional application No. 61/595,296, filed on Feb. 6, 2012, provisional application No. 61/534,453, filed on Sep. 14, 2011.

(51) Int. Cl.
| | |
|---|---|
| A61B 17/70 | (2006.01) |
| A61B 17/86 | (2006.01) |
| A61B 17/88 | (2006.01) |
| A61B 17/56 | (2006.01) |

(52) U.S. Cl.
CPC ...... *A61B 17/7034* (2013.01); *A61B 17/7032* (2013.01); *A61B 17/7049* (2013.01); *A61B 17/7053* (2013.01); *A61B 17/7076* (2013.01); *A61B 17/8605* (2013.01); *A61B 17/8685* (2013.01); *A61B 17/8869* (2013.01);
(Continued)

(58) Field of Classification Search
CPC ..................... A61B 17/7034; A61B 17/7032
See application file for complete search history.

(56) References Cited

U.S. PATENT DOCUMENTS

| | | |
|---|---|---|
| 2,001,091 A | 5/1935 | Carlson et al. |
| 2,014,091 A | 9/1935 | Shepard et al. |

(Continued)

FOREIGN PATENT DOCUMENTS

| | | |
|---|---|---|
| WO | 0209604 | 2/2002 |
| WO | WO2009025966 A1 | 2/2009 |

*Primary Examiner* — Ellen C Hammond
*Assistant Examiner* — Stuart S Bray
(74) *Attorney, Agent, or Firm* — McNees Wallace & Nurick, LLC

(57) ABSTRACT

A clamp housing assembly and method for providing stabilization as a bone anchor during an operation. The assembly includes a housing, a locking element and a band. The housing defines a longitudinal axis, a center recess, and at least one slot. The housing has two opposing arms extending from a base. At least a portion of the inside surface of each arm may be threaded and at least a portion of the outside surface of each arm may be planar. The locking element is positionable within the recess in a co-axial relationship to the housing. The band is sized for travel along a predetermined path defined in part by the at least one slot in the housing.

23 Claims, 30 Drawing Sheets

(52) U.S. Cl.
CPC .......... *A61B 17/56* (2013.01); *A61B 17/7035* (2013.01); *A61B 17/7077* (2013.01)

(56) References Cited

U.S. PATENT DOCUMENTS

| | | | |
|---|---|---|---|
| 2,049,361 A | 7/1936 | Ericsson | |
| 4,443,915 A | 4/1984 | Niemeyer | |
| 4,570,618 A | 2/1986 | Wu | |
| 4,716,630 A | 1/1988 | Skyba | |
| 5,092,866 A | 3/1992 | Breard et al. | |
| 5,133,111 A | 7/1992 | Brown | |
| 5,161,351 A | 11/1992 | Woodruff | |
| 5,291,638 A | 3/1994 | Huang | |
| 5,380,326 A | 1/1995 | Lin | |
| 5,395,374 A * | 3/1995 | Miller | A61B 17/8861 606/103 |
| 5,772,663 A | 6/1998 | Whiteside et al. | |
| RE36,221 E | 6/1999 | Breard et al. | |
| 5,920,963 A | 7/1999 | Chou | |
| 5,935,133 A * | 8/1999 | Wagner | A61B 17/82 606/103 |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,228,096 B1 | 5/2001 | Marchand | |
| 6,290,700 B1 | 9/2001 | Schmotzer | |
| 6,296,643 B1 | 10/2001 | Hopf et al. | |
| 6,325,802 B1 | 12/2001 | Frigg | |
| 6,391,030 B1 | 5/2002 | Wagner et al. | |
| 6,415,480 B1 | 7/2002 | Kane et al. | |
| 6,436,099 B1 | 8/2002 | Drewry et al. | |
| 6,641,584 B2 | 11/2003 | Hashimoto et al. | |
| 6,682,533 B1 | 1/2004 | Dinsdale et al. | |
| 6,689,140 B2 | 2/2004 | Cohen | |
| 7,207,090 B2 | 4/2007 | Mattchen | |
| 7,334,301 B2 | 2/2008 | Huang | |
| 7,367,978 B2 | 5/2008 | Drewry et al. | |
| 7,444,720 B2 | 11/2008 | Huang | |
| 7,468,067 B2 | 12/2008 | Licata et al. | |
| 7,524,324 B2 | 4/2009 | Winslow et al. | |
| 7,824,430 B2 | 11/2010 | Allard et al. | |
| 7,901,436 B2 | 3/2011 | Baccelli | |
| 8,257,367 B2 | 9/2012 | Bryant et al. | |
| 8,469,966 B2 | 6/2013 | Allen et al. | |
| 9,039,711 B2 | 5/2015 | Mickiewicz et al. | |
| 2001/0034522 A1 | 10/2001 | Frigg | |
| 2002/0072753 A1 * | 6/2002 | Cohen | A61B 17/8861 606/103 |
| 2004/0138666 A1 | 7/2004 | Molz, IV et al. | |
| 2006/0036255 A1 * | 2/2006 | Pond | A61B 17/7079 606/86 R |
| 2006/0217726 A1 | 9/2006 | Maxy et al. | |
| 2006/0229623 A1 | 10/2006 | Bonutti et al. | |
| 2007/0072493 A1 | 3/2007 | Sournac et al. | |
| 2007/0088362 A1 | 4/2007 | Bonutti et al. | |
| 2007/0167949 A1 * | 7/2007 | Altarac | A61B 17/7032 606/86 A |
| 2007/0203491 A1 | 8/2007 | Pasquet et al. | |
| 2007/0226961 A1 | 10/2007 | Anderson et al. | |
| 2007/0288026 A1 * | 12/2007 | Shluzas | A61B 17/02 606/86 A |
| 2008/0058818 A1 | 3/2008 | Schwab | |
| 2008/0140122 A1 | 6/2008 | Bethell | |
| 2008/0255576 A1 * | 10/2008 | Protopsaltis | A61B 17/7091 606/104 |
| 2008/0262551 A1 * | 10/2008 | Rice | A61B 17/8869 606/268 |
| 2008/0275469 A1 | 11/2008 | Fanton et al. | |
| 2009/0105715 A1 * | 4/2009 | Belliard | A61B 17/8869 606/103 |
| 2009/0131982 A1 | 5/2009 | Schwab | |
| 2009/0138048 A1 * | 5/2009 | Baccelli | A61B 17/8869 606/263 |
| 2009/0198273 A1 * | 8/2009 | Zhang | A61B 17/7034 606/205 |
| 2009/0281575 A1 | 11/2009 | Carls et al. | |
| 2009/0292317 A1 | 11/2009 | Belliard | |
| 2010/0094302 A1 * | 4/2010 | Pool | A61B 17/7004 606/90 |
| 2010/0106195 A1 | 4/2010 | Serhan et al. | |
| 2010/0249845 A1 * | 9/2010 | Meunier | A61B 17/7011 606/263 |
| 2010/0275420 A1 | 11/2010 | Huang | |
| 2011/0112581 A1 | 5/2011 | Clement | |
| 2011/0152950 A1 | 6/2011 | Baccelli | |
| 2011/0218573 A1 * | 9/2011 | Ferree | A61B 17/7032 606/263 |
| 2011/0301644 A1 * | 12/2011 | Belliard | A61B 17/7008 606/263 |
| 2012/0130373 A1 | 5/2012 | Larroque-Lahitette | |
| 2013/0035726 A1 | 2/2013 | Nguyen et al. | |
| 2013/0041410 A1 * | 2/2013 | Hestad | A61B 17/7032 606/263 |
| 2013/0072983 A1 * | 3/2013 | Lindquist | A61B 17/7049 606/278 |
| 2013/0245691 A1 | 9/2013 | Hutton et al. | |
| 2013/0261668 A1 | 10/2013 | Douget et al. | |
| 2013/0268011 A1 * | 10/2013 | Rezach | A61B 17/7053 606/86 A |
| 2013/0325070 A1 | 12/2013 | Larroque-Lahitette et al. | |
| 2014/0114356 A1 | 4/2014 | Le Couedic et al. | |
| 2014/0257398 A1 * | 9/2014 | Baccelli | A61B 17/7053 606/263 |
| 2014/0257400 A1 | 9/2014 | George et al. | |
| 2014/0257401 A1 | 9/2014 | George et al. | |
| 2014/0277149 A1 | 9/2014 | Rooney et al. | |
| 2014/0277207 A1 * | 9/2014 | Baccelli | A61B 17/8869 606/86 A |
| 2016/0183983 A1 * | 6/2016 | Heflin | A61B 17/7037 606/266 |

\* cited by examiner

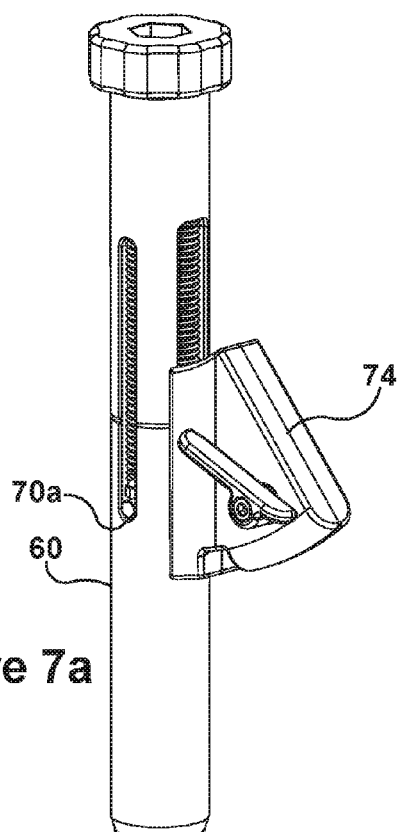
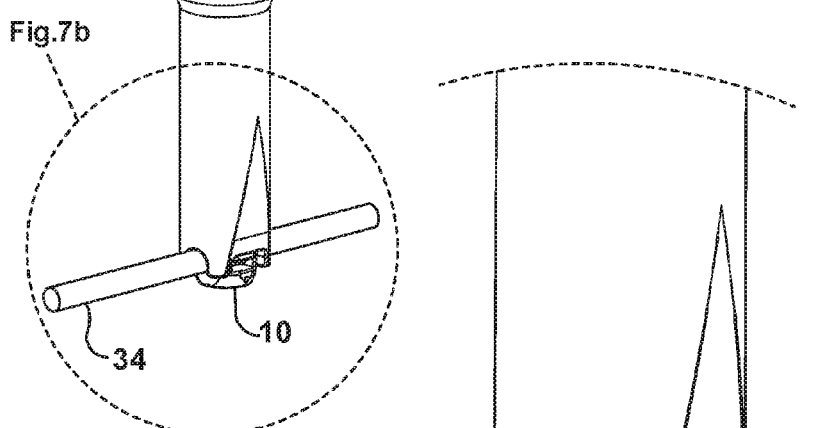
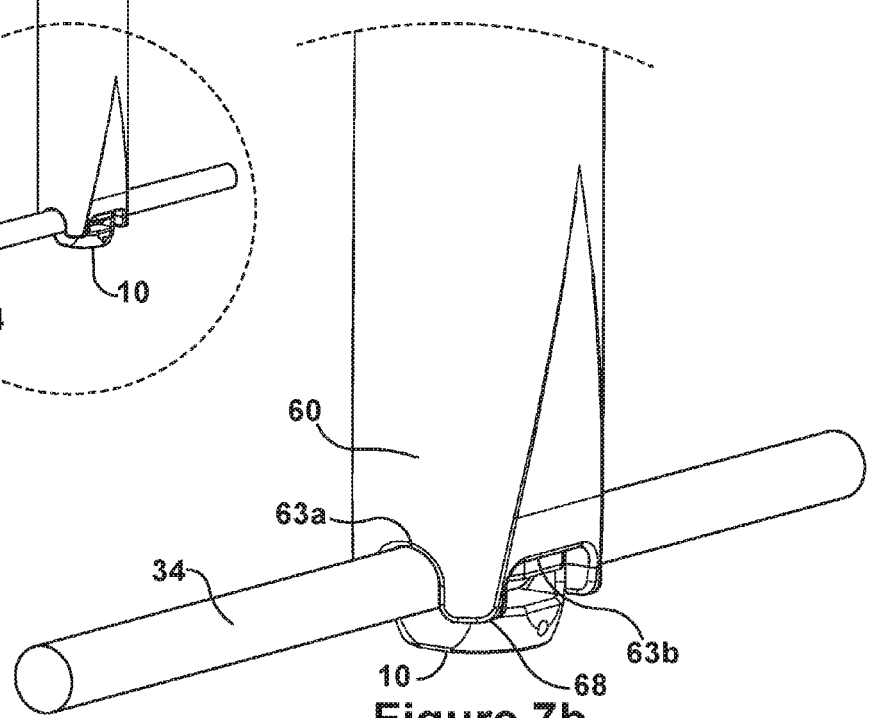

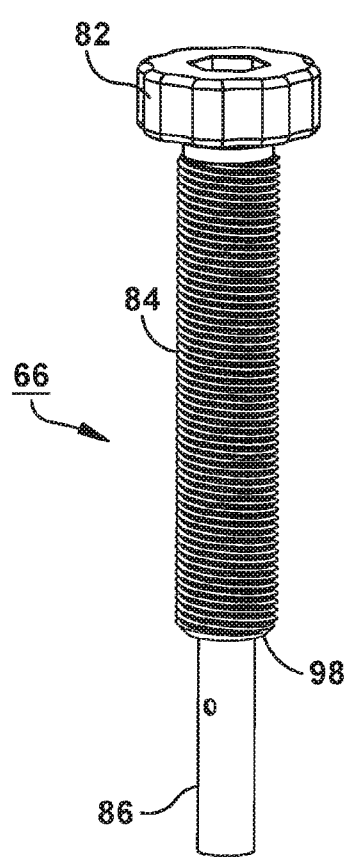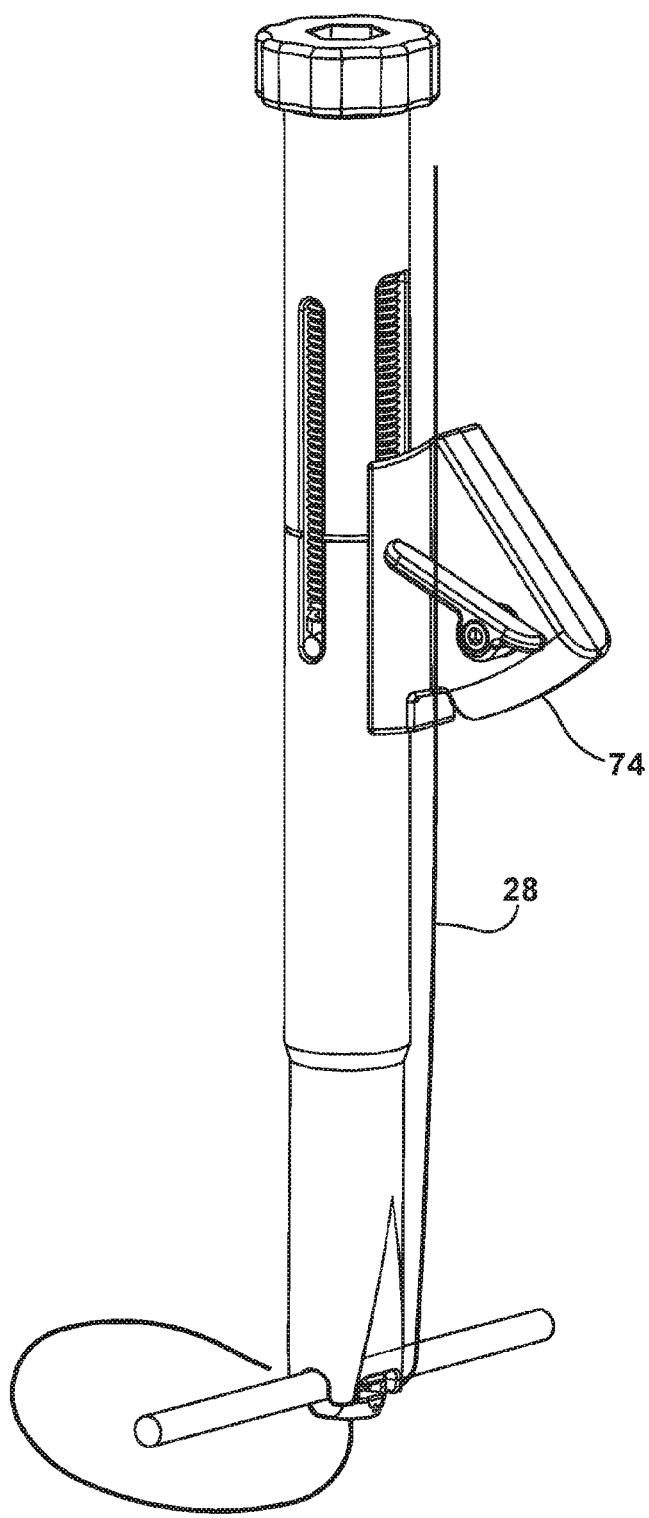
Figure 7g
Figure 8

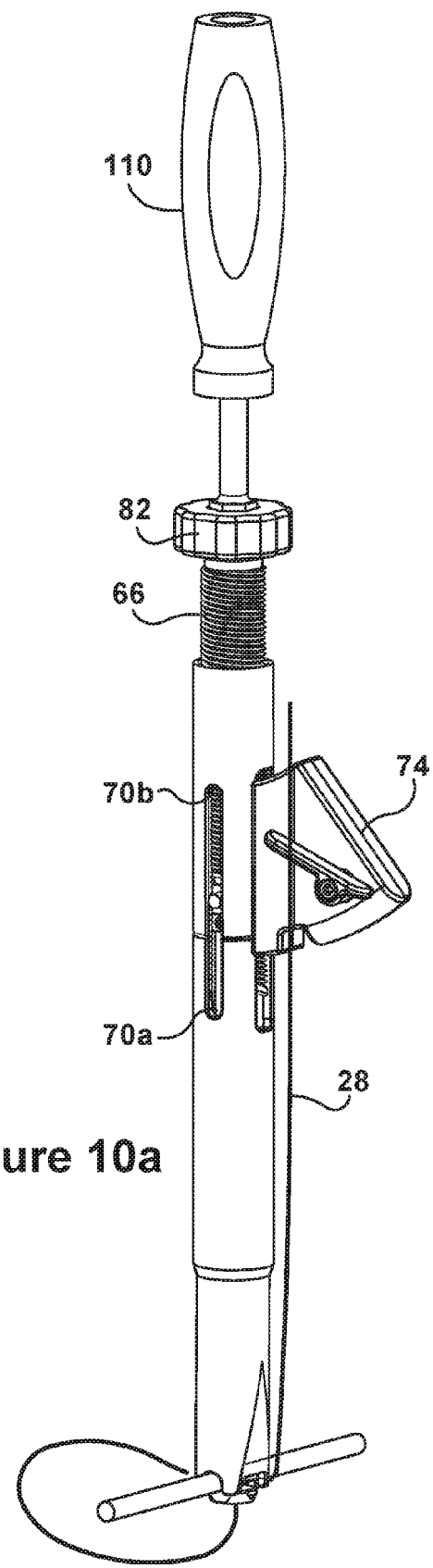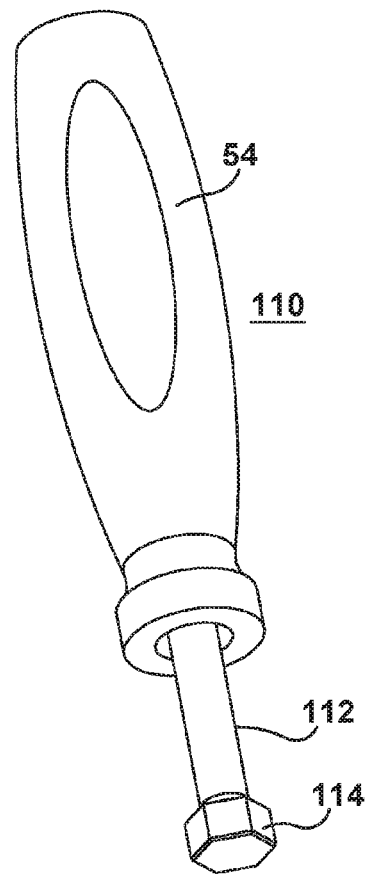
Figure 10a
Figure 10b

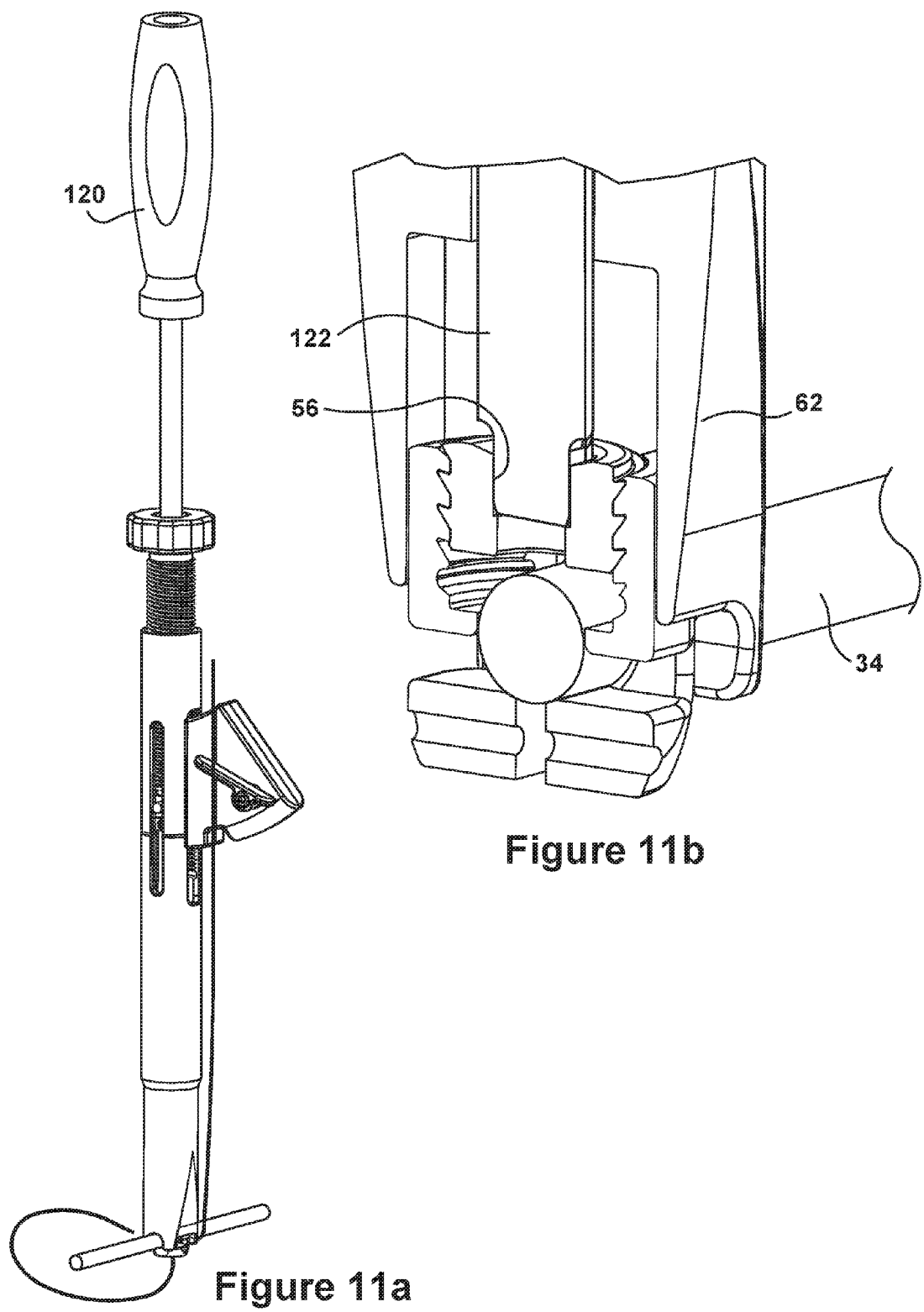

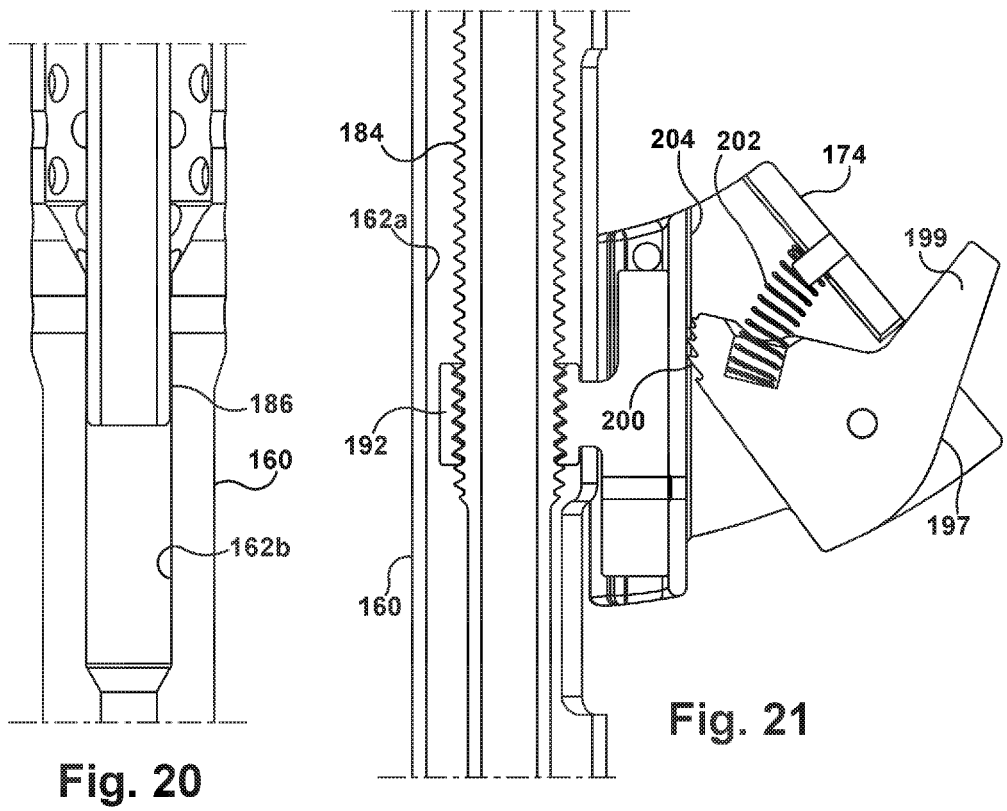

TETHER CLAMP AND IMPLANTATION SYSTEM

CROSS-REFERENCE TO RELATED APPLICATION

This non-provisional application is a continuation of U.S. Non-Provisional patent application Ser. No. 13/618,724, entitled TETHER CLAMP AND IMPLANTATION SYSTEM, filed Sep. 14, 2012, now U.S. Pat. No. 9,173,685, issued on Nov. 3, 2015, and claims priority to U.S. Non-Provisional patent application Ser. No. 14/746,226, filed Jun. 22, 2015, which is pending, each of which claims the benefit of U.S. Provisional Patent Application Ser. No. 61/534,453, entitled TETHER CLAMP AND IMPLANTATION SYSTEM, filed Sep. 14, 2011, and U.S. Provisional Patent Application Ser. No. 61/595,296, entitled TETHER CLAMP AND IMPLANTATION SYSTEM, filed Feb. 6, 2012, the entire disclosure of each of which applications is incorporated herein by reference, to the extent that said disclosures do not conflict with the present application.

BACKGROUND

The human skeleton is formed of bones, each bone performing a structural role, either individually or collectively with other bones. For example, the spine is made up of approximately 24 vertebrae, each composed of several portions, which act as a whole to surround and protect the spinal cord and nerves, provide structure to the body and enable fluid body motion in many planes. The vertebrae are normally aligned along an axis, with each vertebra presenting a posterior wall from which projects a spinous process and two side edges having walls from which project the ribs and/or transverse processes.

An individual's spine may be damaged or otherwise compromised in one of many ways. A spine may present an abnormal curvature, such as for example, vertebrae inclined and rotated relative to one another and relative to the vertebral axis. In such a curvature, the lateral edges of the vertebrae situated on one side are closer to one another and form a concave curve, while the lateral edges on the other side are spaced apart from one another and form a convex curve. This condition can result in subsequent and serious conditions, such as for example, abnormalities of the cardiac, pulmonary, neuromuscular and gastrointestinal systems.

An individual's spine may also be damaged by one or more fractured vertebrae. Spine osteosynthesis, the reduction (bringing together) and fixation of a bone fracture with implantable devices, is a known treatment of a spinal fracture. Specifically, osteosynthesis is a surgical procedure with an open or percutaneous approach to the fractured bone, which aims to bring the fractured bone ends together and immobilize the fracture site while healing takes place.

To correct these and other conditions, conventional procedures have been developed using mechanical implants to straighten or otherwise hold successive vertebrae in a fixed position. To keep the vertebrae in the desired relative position, hardware, such as a screw, is inserted into the vertebrae. The screws include tulip heads and act as an anchoring point for a connecting member between vertebrae, such as a straight surgical rod.

The use of screws introduces risk into the surgical procedure and may cause additional damage to the vertebrae. Spinal clamps have been developed that provide additional anchor points along the spine when the use of a screw is not possible or not optimal. Known exemplary spinal clamps introduce further risk and complexity into the surgery, including installation complexity, inadequate size offerings and additional parts.

Similar risk and complexity exist in orthopedic surgery in other areas of the body adjacent or remote from the spine.

SUMMARY

The present application describes various exemplary methods and apparatus for a spinal clamp, specifically, a tether clamp installation system.

In an embodiment, a spinal clamp assembly includes a clamp housing, a locking element, and a band. The clamp housing may be a one piece base, have no moving parts, and defines at least one slot for passage of the band. The housing is adapted to receive a surgical rod without the use of a retaining clip or other hardware beyond the locking element. The locking element may be positioned co-axial with the housing. During installation, the band is tightened around a vertebra and tensioned into a tightened position by a tensioning instrument.

In another embodiment, a spinal clamp system includes a spinal clamp assembly, locking and tensioning tools, and a tensioning instrument. The tensioning instrument has a distal end which engages the spinal clamp assembly. The tensioning instrument further defines at least one slot which allows movement of a carriage between a non-tightened position and a tightened position, permitting a surgeon to tighten the band. A longitudinal cylinder of the tightening instrument permits the insertion of various tools, e.g., to restrict movement of the vertebral structure relative to the implant rod.

An embodiment of a method of implanting a spinal clamp assembly along at least two vertebrae includes: providing a spinal clamp assembly including a clamp housing, a locking element, a band, and a surgical rod; positioning the housing along the rod at a desired location adjacent a vertebra; wrapping a band about a lamina and through the housing; inserting the locking element within the housing to capture the rod; provisionally locking the locking element; engaging a tensioning instrument with the spinal clamp assembly; inserting the band through a carriage of the tensioning instrument; moving the carriage to a tightened position to secure the band; and locking the locking element.

BRIEF DESCRIPTION OF THE DRAWINGS

Features and advantages of the general inventive concepts will become apparent from the following detailed description made with reference to the accompanying drawings.

FIG. 1b is a side perspective view of the housing of FIG. 1a;

FIG. 1c is a front view of a band wrapped about the housing of FIG. 1a;

FIG. 1d is a bottom perspective view of the housing of FIG. 1a;

FIG. 5b is an enlarged perspective view of the designated circular area of FIG. 5a;

FIG. 5c is a perspective view of the provisional locking tool of FIG. 5a;

FIG. 6b is a rear view of the tensioning instrument of FIG. 6a;

FIG. 7a is a front perspective view of the tensioning instrument of FIG. 6a, shown engaged with the rod and spinal clamp assembly of FIG. 5a;

FIG. 7b is an enlarged perspective view of the designated circular area of FIG. 7a;

FIG. 7e is a perspective cross-sectional view of a center portion of the tensioning instrument of FIG. 7a;

FIG. 7f is an enlarged perspective view of a bearing ring of the tensioning instrument of FIG. 7a;

FIG. 7g is a front perspective view of a tightening rod of the tensioning instrument of FIG. 7a;

FIG. 8 is a perspective view of FIG. 7a, shown with the band routed through a carriage of the tensioning instrument, with the carriage in a non-tightened position;

FIG. 9b is a front cross-sectional view of the carriage of FIG. 9a;

FIG. 10a is a perspective view of FIG. 8, shown with the carriage in a tightened position;

FIG. 10b is perspective view of a tightening tool of FIG. 10a;

FIG. 11a is a perspective view of FIG. 10a, shown with the carriage in a tightened position and a screwdriver tool inserted within the tensioning instrument;

FIG. 11b is an enlarged cross-sectional view of the screwdriver tool engaging the set screw;

FIG. 11c is a side view of the screwdriver tool of FIG. 11a;

FIG. 20 is a cross-sectional view of a center portion of the tensioning instrument of FIG. 15;

FIG. 21 is a cross-sectional view of a center portion of the tensioning instrument of FIG. 15, shown with the tightening rod installed and the carriage in a non-tightened position;

DETAILED DESCRIPTION

Figure 1A:
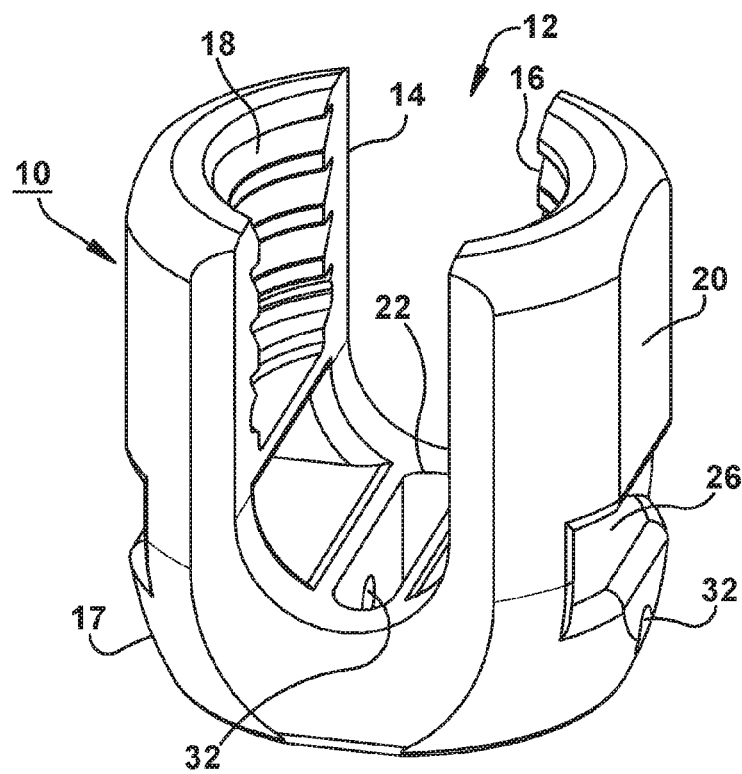
FIG. 1a is a front perspective view of a spinal clamp housing.

This Detailed Description merely describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the present invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The invention is directed a tether clamp and implantation system for use in orthopedic surgery. The system provides a temporary implant intended to provide temporary stabilization as a bone anchor during the development of solid bony fusion and aid in the repair of bone fractures. Exemplary indications for use include, but are not limited to, the following applications:
1. Spinal trauma surgery, used in sub-laminar, interspinous, or facet wiring techniques.
2. Spinal reconstructive surgery, incorporated into constructs for the purpose of correction of spinal deformities such as scoliosis, kyphosis, spondylolisthesis.
3. Spinal degenerative surgery, as an adjunct to spinal fusions.
4. Treatment of idiopathic and neuromuscular scoliosis in patients eight years of age and older.

The inventive system may also be used in conjunction with other medical implants made of metal, for example, titanium alloy or cobalt chromium alloy, whenever "wiring" may help secure the attachment of other implants.

An embodiment of the invention which will now be discussed is a spinal clamp implant. The spinal implant is used to aid in fusion and stabilization in one or more vertebrae during a posterior access surgery. The spinal clamp can be used with one or more similar spinal clamps to provide anchoring points for a surgical rod. The spinal clamp can further be used with conventional screw and tulip head implants. For example, the spinal clamp may be secured to third lumbar vertebra L3, while conventional screw and tulip head implants are secured to the second lumbar vertebra L2 and the fourth lumbar vertebra L4. When discussing the spinal clamp and implantation of the spinal clamp, the terms "proximal" and "distal" are used relative to the surgeon, and not the operating field, i.e., not relative the patient.

An embodiment of this invention was discussed in U.S. Provisional Patent Application Ser. No. 61/534,453, entitled TETHER CLAMP AND IMPLANTATION SYSTEM and filed Sep. 14, 2011, the entire disclosure of which is incorporated herein by reference.

Figure 1B:
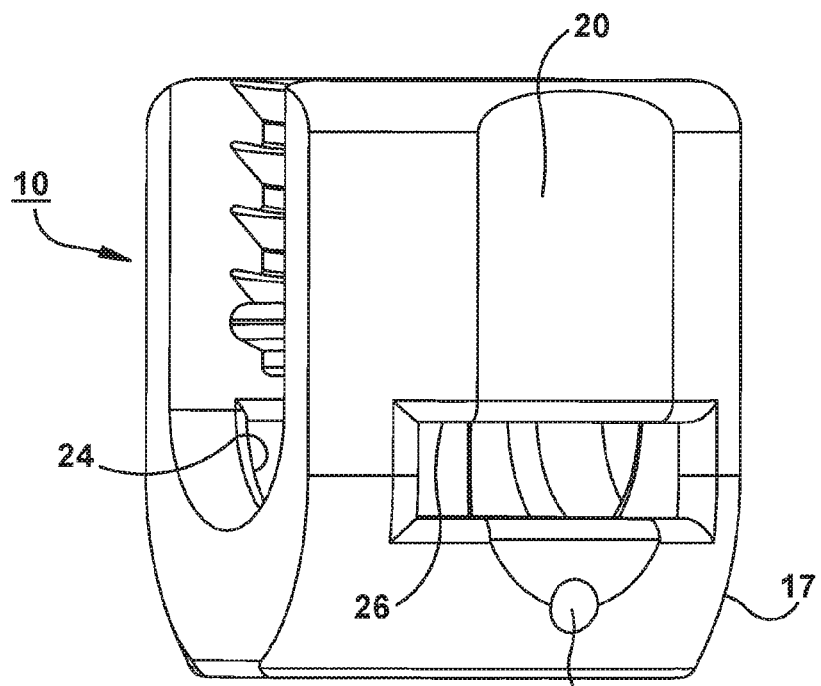

Referring now to the drawings, a spinal clamp housing 10 is shown in FIGS. 1a and 1b. The housing is adapted for placement at a desired implantation point adjacent to a vertebra. The housing 10 may be constructed of suitable material, such as for example, stainless steel, cobalt chromium, or titanium.

Figure 3:
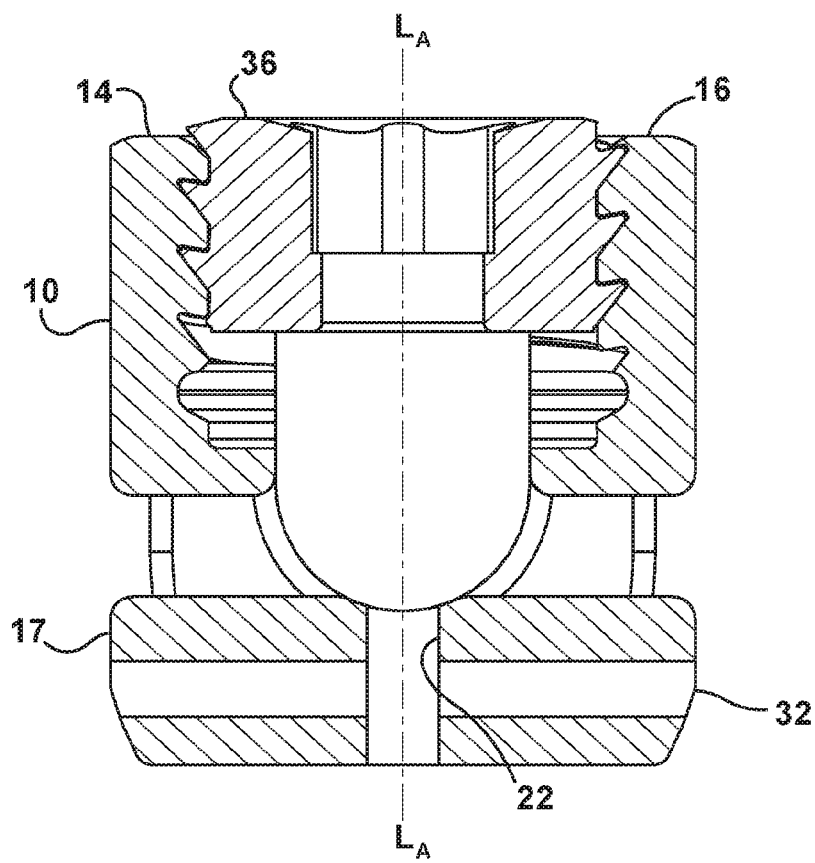
FIG. 3 is a front cross-sectional view of a set screw positioned within the housing of FIG. 1a, shown without a rod or band.

The housing is generally cylindrical shaped and defines a longitudinal axis $L_A$ (best seen in FIG. 3). More specifically, the housing includes a center recess 12 defined by opposing arms 14, 16 extending from a base 17. An internal surface of the arms 14, 16 include a mating engagement surface, such as for example, a threaded surface 18. The threaded surface mates with a locking element, such as for example, a set screw, a blocking nut, or a blocker. An exterior of the exemplary arms 14, 16 include a flat surface 20. A tightening instrument engages the flat surface 20 to prevent housing 10 rotation while the set screw is rotated into a locked position. This operation will be discussed in further detail. It should be apparent to one with skill in the art that other styles, types, and sizes of surfaces for locking elements and tensioning instrument mating can be used in the practice of this invention.

Figure 1C:
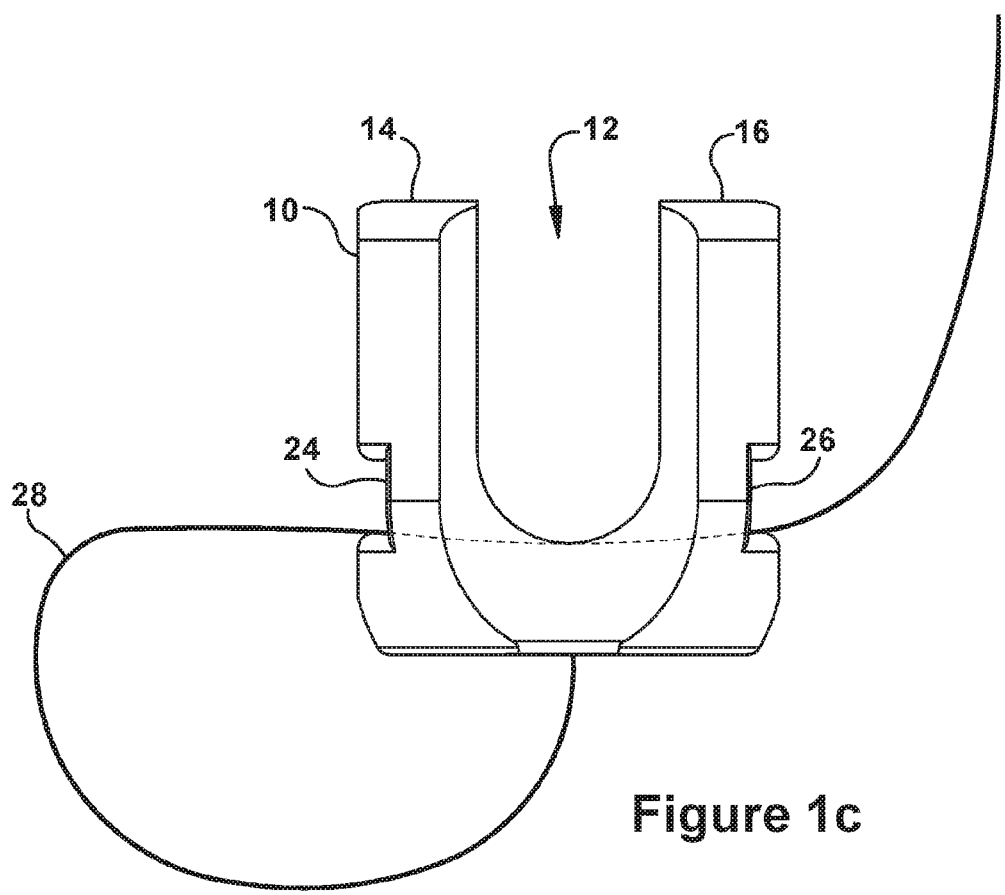

The housing 10 includes structural features to permit a band to be wrapped securely about the housing. A first slot 22 is located at the bottom of the recess 12 and defines a passage for a band along a longitudinal axis of the housing. The first slot may allow use by a surgeon as a starting point for band travel within and in the vicinity of the housing 10. For example, a knot may be tied at the beginning of the band to prohibit one end of the band from entering the slot and passing through to the bottom side of the housing, or one end of the band may include a clip larger in size than the slot 22. A second slot 24 and a third slot 26 are formed in opposing positions on either side of the housing 10. These slots 24, 26 may permit band travel perpendicular to the longitudinal axis of the housing 10. An exemplary travel path of a band 28 is illustrated in FIG. 1c. The band 28 is illustrated in an exemplary pattern, for example, routed in a pattern around a lamina (not shown).

The housing 10 further includes apertures 32. These apertures may be used by a surgeon for various purposes, such as for example, grasping the housing 10 during implantation, or insertion of a pin for a structural anchor for another assembly piece, such as for example, the tether band.

Figure 1D:
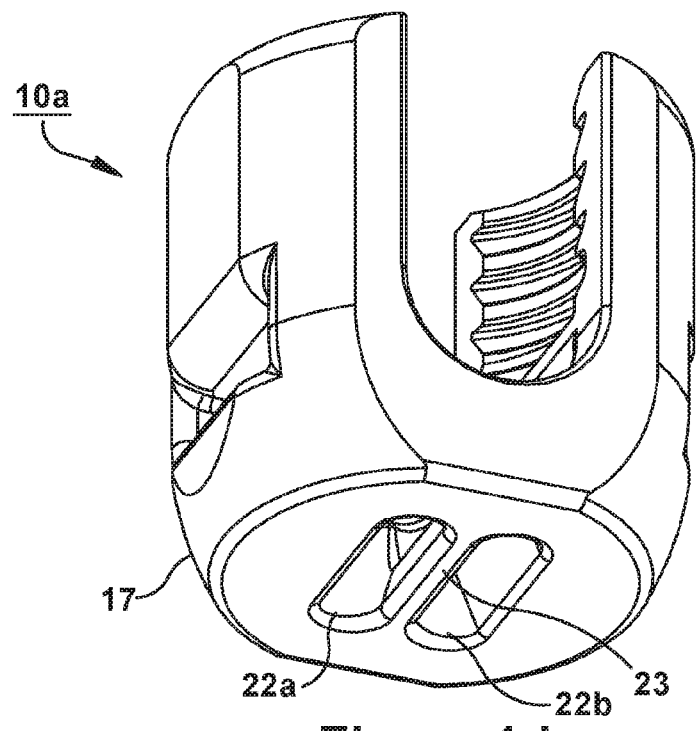
Figure 1E:
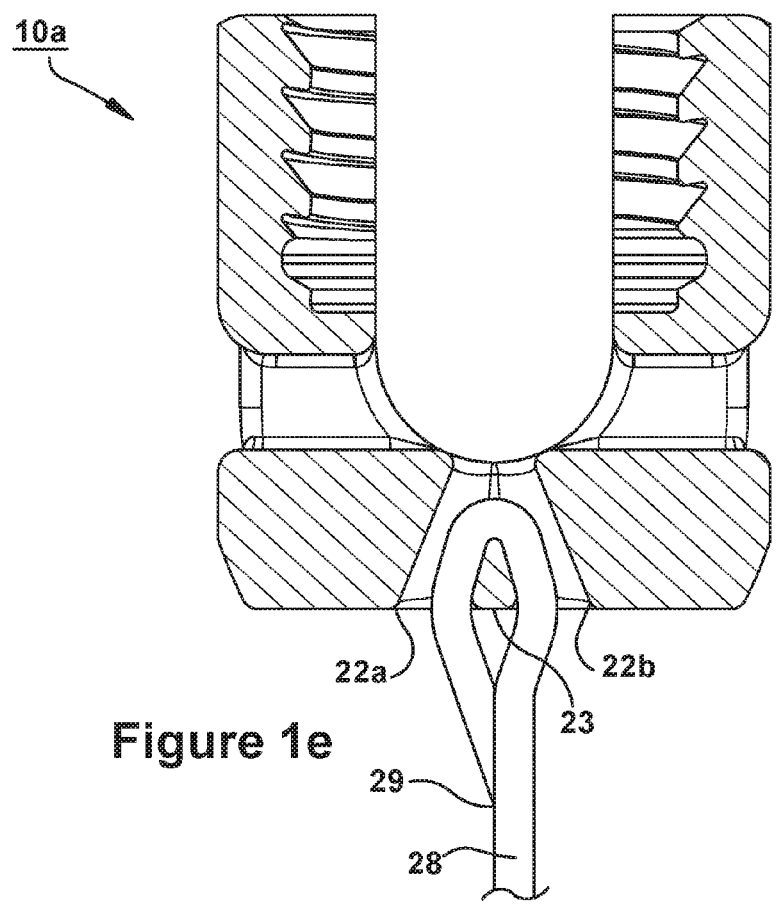
FIG. 1e is a front cross-sectional view of a band engaged with the housing of FIG. 1d.

Structural features of the bottom of the spinal clamp housing are best seen in FIG. 1d. In this embodiment, the housing 10a includes two slots 22a, 22b, separated by a bridge 23, at the bottom of the housing recess. The slots 22a, 22b may allow use by a surgeon as a starting point for band travel within and in the vicinity of the housing 10a. For example, a first end of the band 28 may be routed through both slots as shown in FIG. 1e, and secured to a distal location 29 of the band, to secure the band to the housing 10a. In the exemplary embodiment, the band is integral to the housing and secured prior to surgery, for example, during surgery preparation or by a manufacturer. In other embodiments, the surgeon may attach the first end of the band at the distal location 29 by one of several methods, including sewing the first end to the band. It should be understood by those with ordinary skill in the art that the number of slots used to secure the band, if any, as well as the shape and location of the slots, may vary in the practice of this invention.

Figure 12:
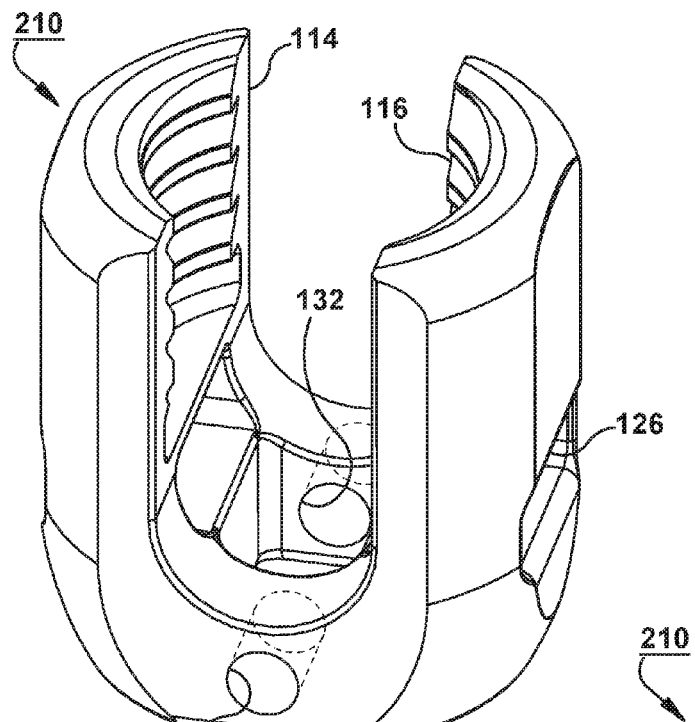
FIG. 12 is a front perspective view of another spinal clamp housing.
Figure 13:
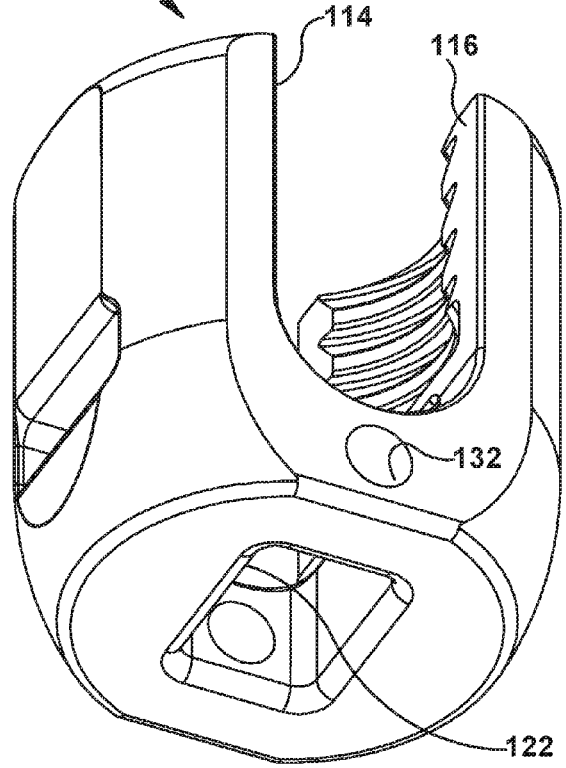
FIG. 13 is a bottom perspective view of the spinal clamp housing of FIG. 12.

Another embodiment of the invention includes a housing having different structural features. Specifically, the housing 210 illustrated in FIGS. 12-14 includes a single aperture 122 at the bottom of housing. The aperture as shown is a rectangular shaped slot. It may be of any suitable shape, width and length. As shown, the single slot 122 is wider than the double slots 22a, 22b shown in the housing 10 of FIG. 1d.

Figure 14:
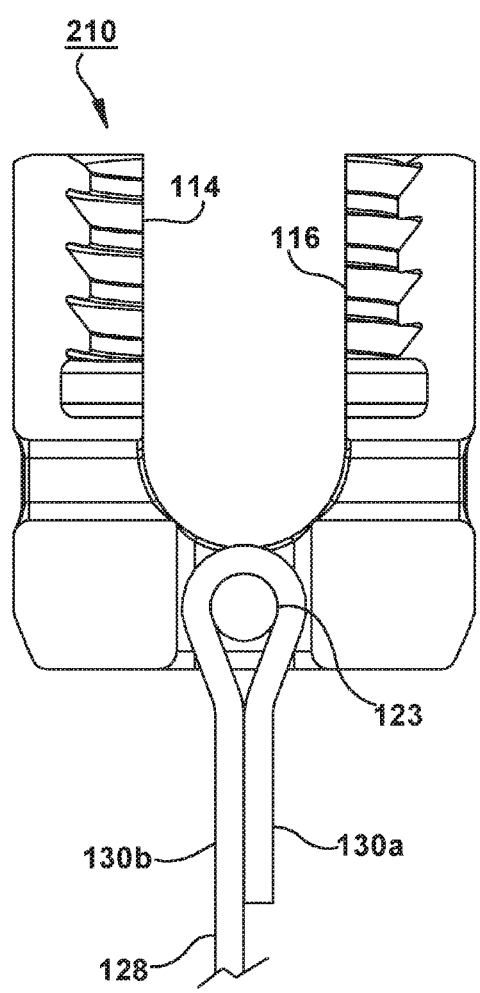
FIG. 14 is a front sectional view of the spinal housing of FIG. 13, show with a pin and band installed in the housing.

The base of the housing 210 is absent any apertures oriented perpendicular to a position of an installed surgical rod. The housing 210 does include two holes 132 for supporting a pin 123 as seen in FIG. 14. The holes are positioned co-axial with an installed position of a surgical rod. The end of the band is fixed to provide a loop for slipping over the pin, or the band may be fixed to the pin. As shown, a loop and the end of a tether band 128 is formed by fixing two band lengths 130a, 130b.

Figure 2:
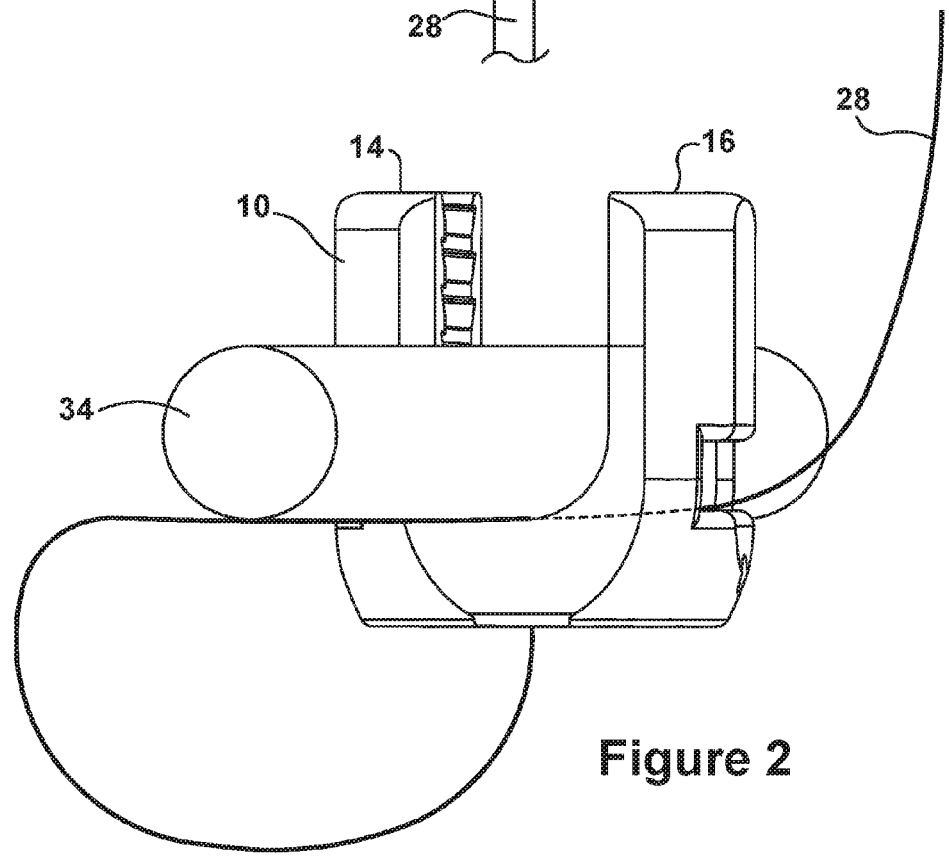
FIG. 2 is a front perspective view of a spinal rod positioned within the housing and band assembly of FIG. 1c.

Referring now to FIG. 2, a surgical rod 34 placed within the recess 12 of the housing is shown. The housing is concave-shaped to accept and laterally retain the rod 34 within the arms 14, 16. The weight of the rod 34 applies a force to pinch a portion of the band 28 against the housing 10.

Figure 4:
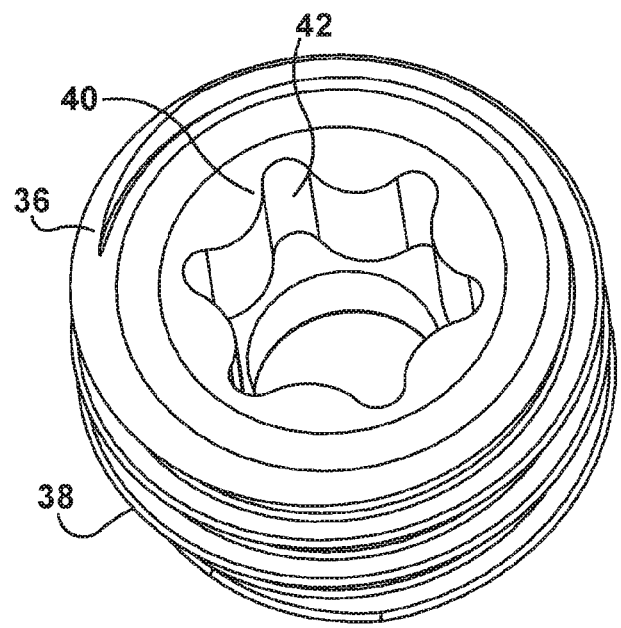
FIG. 4 is a top perspective view of a locking element of FIG. 3.

During implantation, the next step is to provisionally lock the rod in place with use of a set screw. A set screw 36 is shown engaged with a housing 10 in FIG. 3. The rod 34 and band 28 are not shown for clarity. As shown in FIGS. 3 and 4, the set screw 36 has a threaded external circumferential surface 38 which engages the internal threaded surface 18 of the arms 14, 16. A top surface 40 of the set screw 36 includes a cut-out recess 42. The recess 42 is shaped to accept locking tools.

Figure 5A:
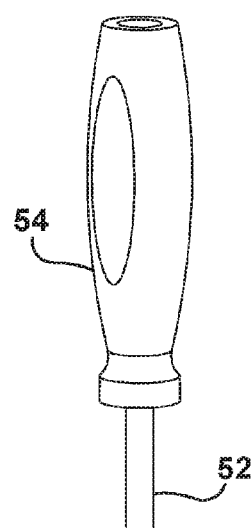
FIG. 5a is a perspective view of a provisional locking tool engaged with a rod and spinal clamp assembly, shown without a band.
Figure 5B:
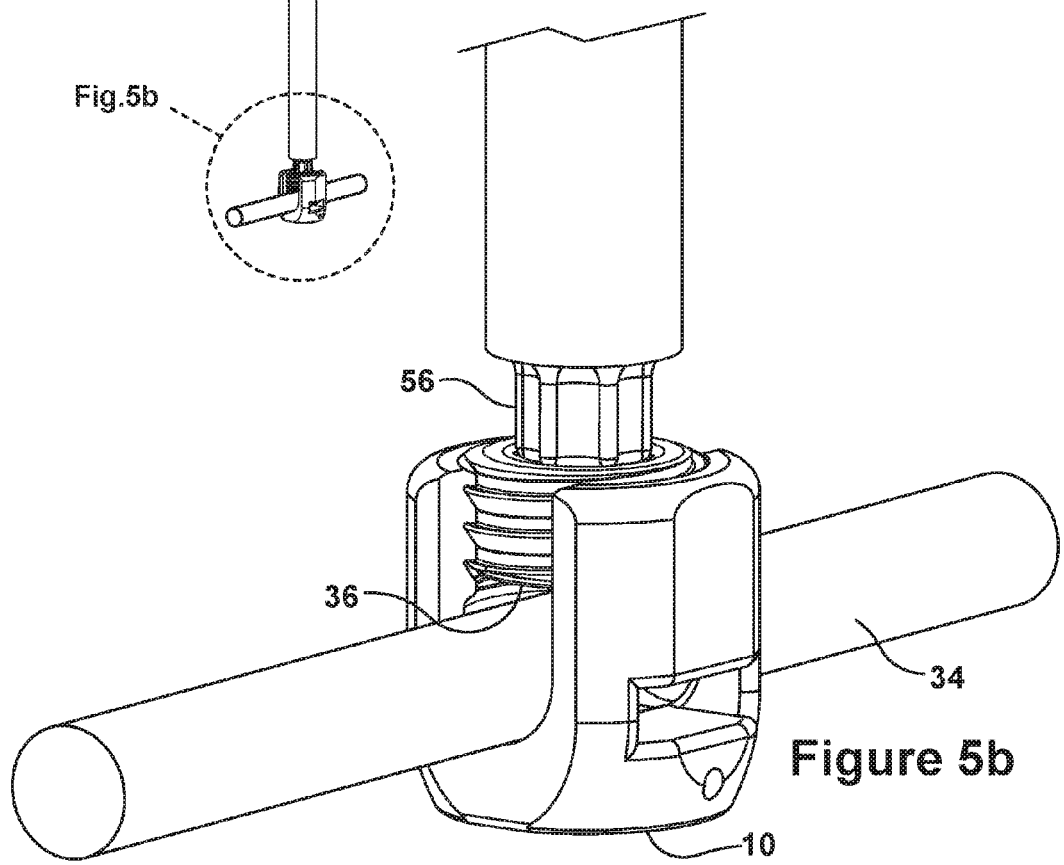

FIGS. 5a and 5b illustrate a provisional locking tool 50 engaged with a set screw 36. In the implantation of the spinal clamp, a surgeon uses the provisional locking tool 50 to tighten the set screw enough to temporarily contain the rod 34. The set screw must not be locked in place until the band is sufficiently tightened about the target lamina. In a further surgical step, the set screw 36 is locked in a final position.

Figure 5C:
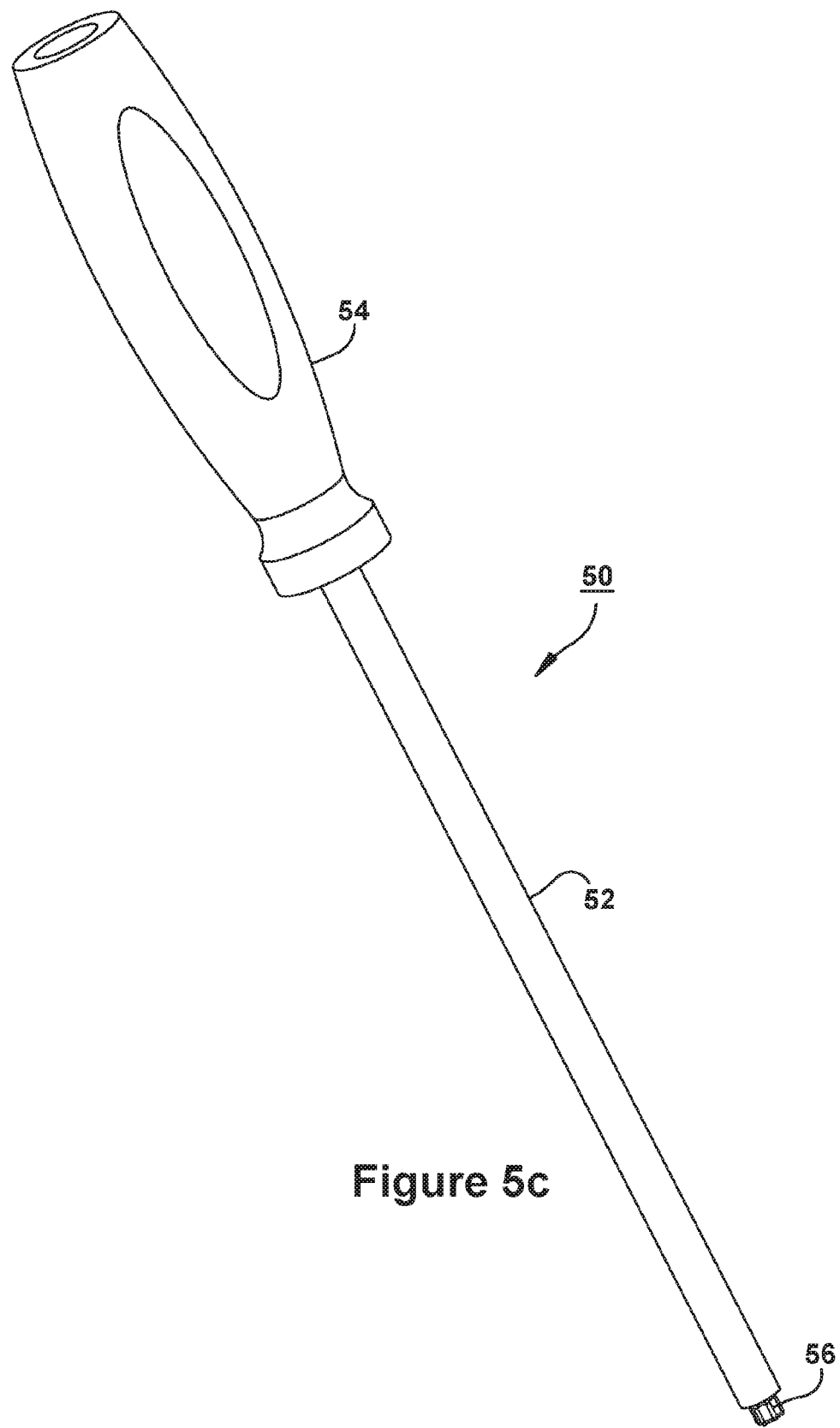

As shown in FIG. 5c, the provisional locking tool 50 includes an instrument rod 52 and palm handle 54. The palm handle 54 may be separable from the instrument rod 52. The system may include multiple tools, each with specifically shaped instrument rods. For example, the instrument rod 52 includes a constant diameter shaft terminating in a socket head 56 sized to mate with the recess 42 of the set screw 36.

Figure 7C:
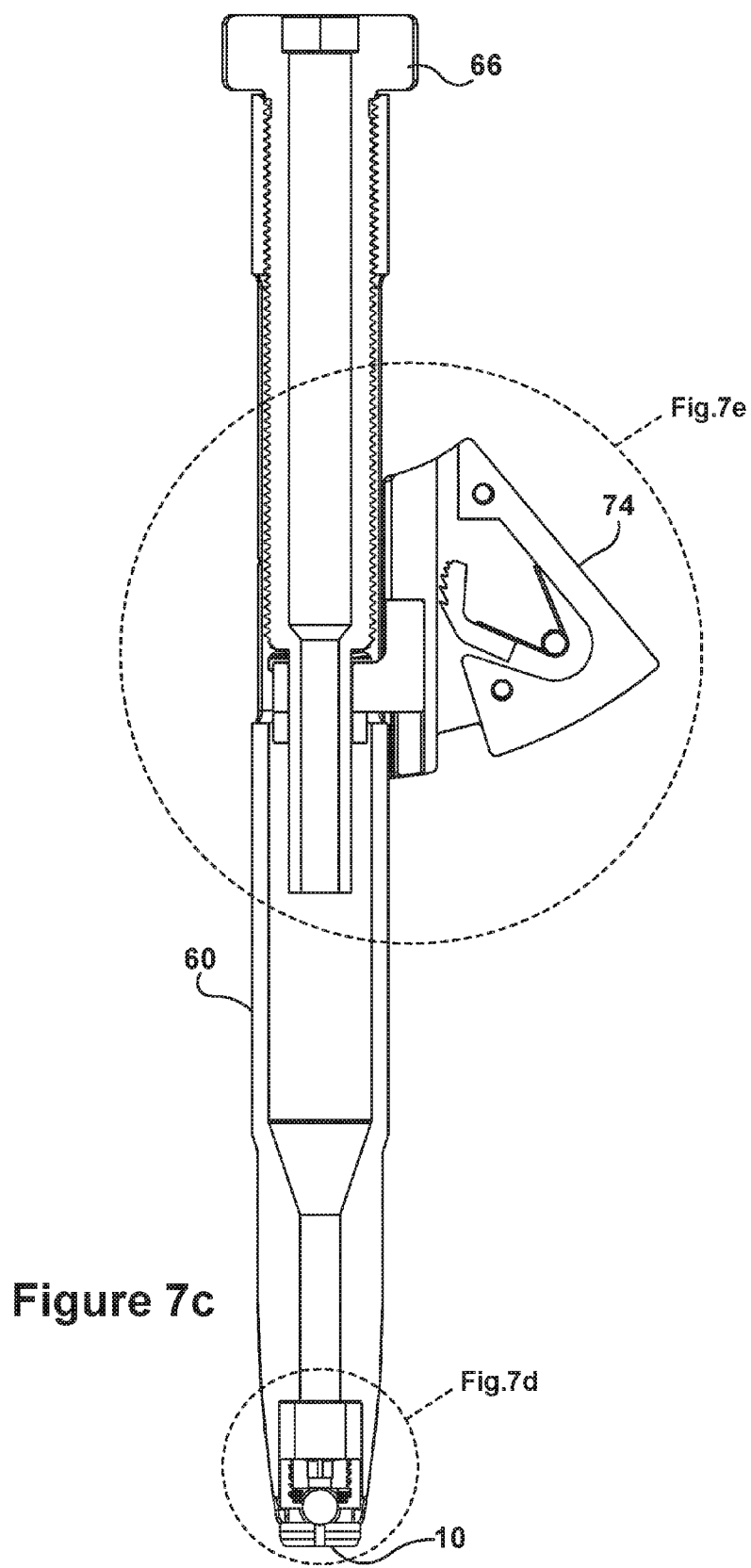
FIG. 7c is a front cross-sectional view of FIG. 7a, shown without a tightening rod.
Figure 7D:
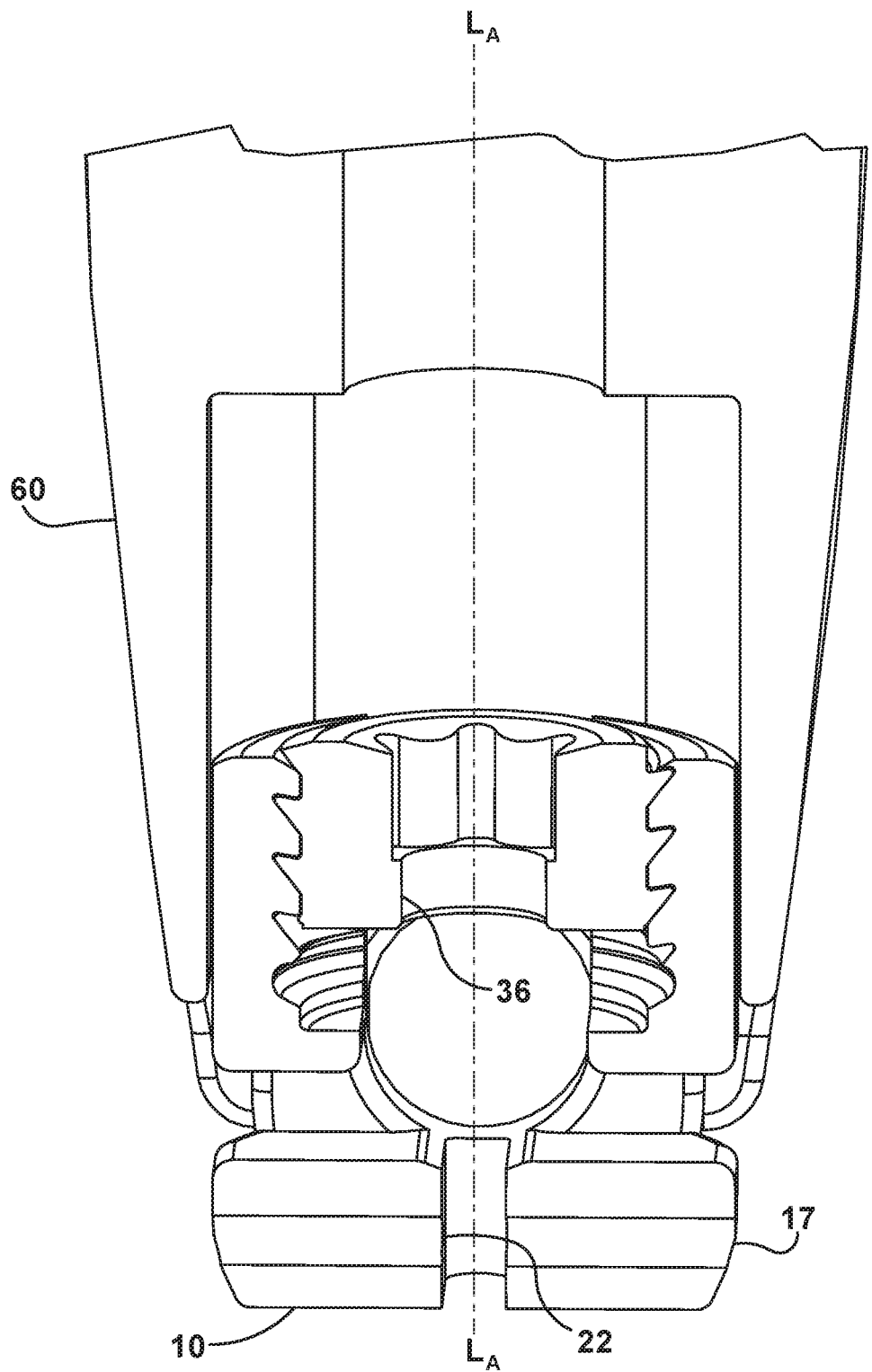
FIG. 7d is an enlarged perspective view of the designated circular area of FIG. 7c.

The spinal clamp installation system includes a tensioning instrument for use by a surgeon to tighten a band and securing the vertebral structure relative to the implant rod. The installation system is arranged for user ease of installation. As shown in the Figures, e.g., FIGS. 3 and 7d, the housing 10, set screw 36 and tensioning instrument 60 are all positionable about a common longitudinal axis $L_A$. Any tools used in the installation, either prior to the engagement of the tensioning instrument, or inserted within the internal channel of the tensioning instrument from a proximal end to a distal end, are also positioned along the same common axis. This arrangement also promotes increased user flexibility, e.g., the user may easily incrementally tighten a band of a spinal clamp assembly, then by retract a tool from the set screw and then disengaging the tensioning instrument from the housing, move to the next sequential spinal clamp assembly along the surgical rod, and make a similar incremental adjustment.

Figure 6A:
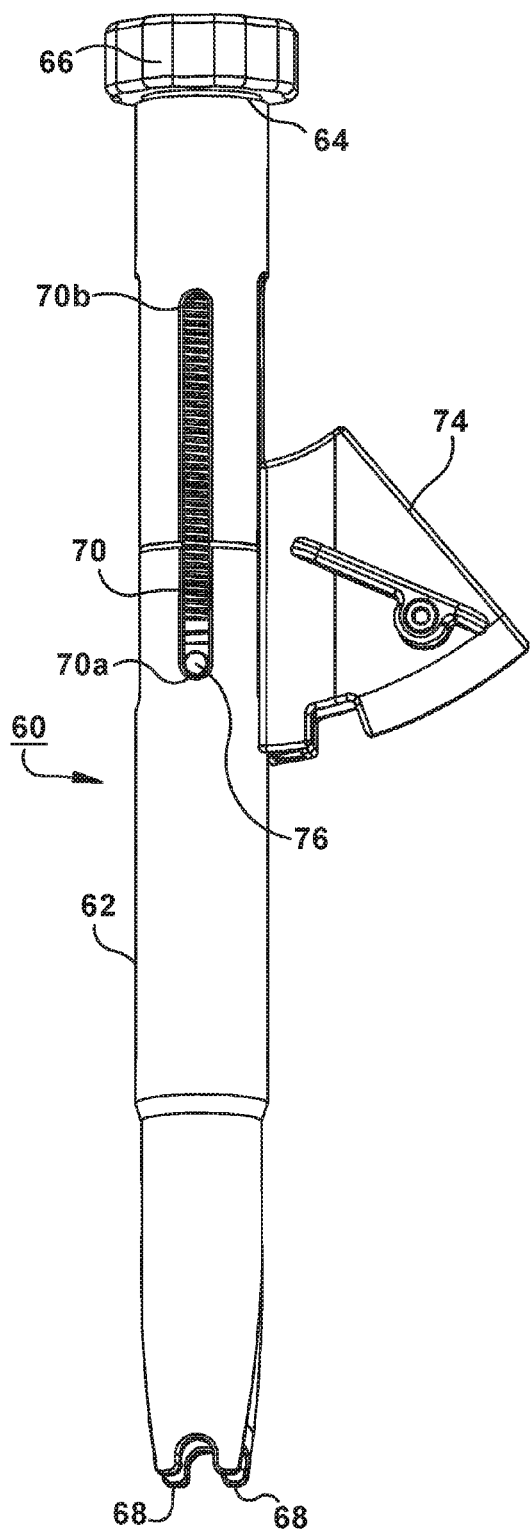
FIG. 6a is a front view of a tensioning instrument.
Figure 6B:
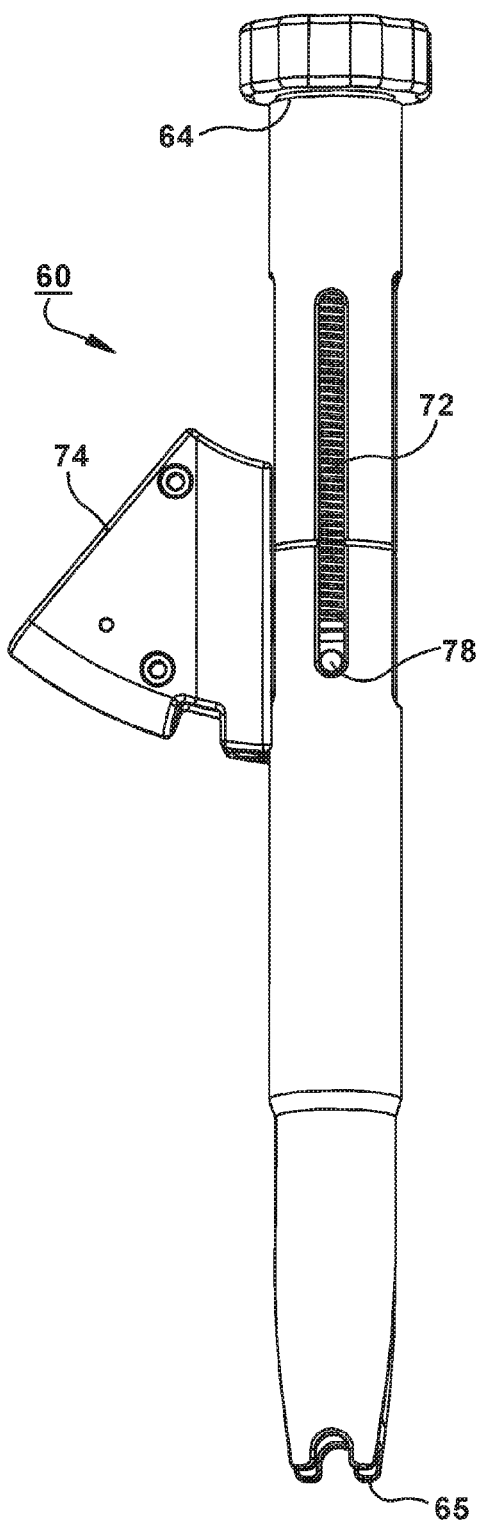

FIGS. 6a and 6b illustrate front and rear views of a tensioning instrument 60. The instrument includes an elongated cylinder 62. The cylinder permits the insertion of tools from a proximal end 64 to a distal end 65 to manipulate the set screw 36, and further contains a hollow tightening rod 66. The tightening rod 66 is used by the surgeon to secure the band 28 in a final position.

The cylinder 62 is adapted for securing the spinal clamp in a final position relative the target vertebra. FIGS. 7a-7d illustrate various views of the tensioning instrument 60 engaged with a spinal rod. The cylinder 62 includes projections 68 at the distal end 65. An arched section 63a between two adjacent projections engage a top surface of the rod 34 (see FIG. 7b). A flat portion 63b between other adjacent projections engage the flat portions 20 on the exterior of the housing 10, to prohibit movement of the housing. The cylinder further defines two opposing slots 70, 72. The slots permit travel of a carriage 74 within the slot, at least partially between a distal end 70a (see FIG. 7a) and proximal end 70b (see FIG. 10a). Two protruding tabs 76, 78 ride within the slots during movement of the carriage. The mechanics of this movement will be discussed in further detail.

Figures 7E, 7F:
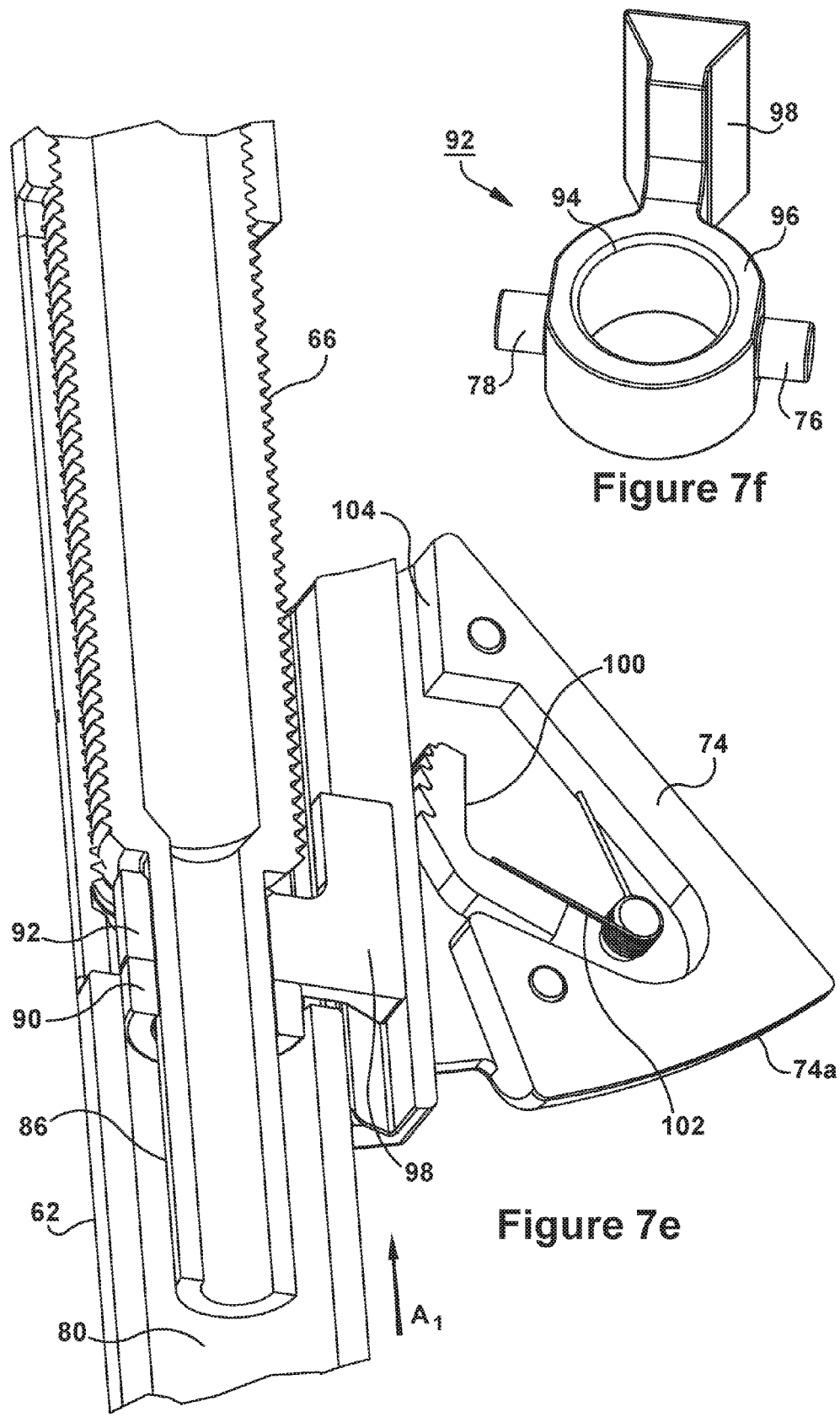

The tensioning instrument is structured to tighten the band 28 to secure the housing 10 to the rod 34. As best seen in FIG. 7e, the cylinder 62 includes an interior surface 80 defining a hollow chamber. Within the proximal portion of the chamber, the tightening rod 66 mates with internal threads of the cylinder. The tightening rod 66 is illustrated in FIG. 7g and includes a knob 82, threaded portion 84, and a distal, non-threaded portion 86. The distal position 86 includes holes 88 for engagement by set screws (not shown) which secure a retaining ring 90 (see FIG. 7e). The retaining ring 90 moves axially within the cylinder as the tightening rod 66 is manipulated by the surgeon.

A bearing ring 92 is disposed to the proximal side of the retaining ring 90, as best shown in FIG. 7e. Further as shown in FIG. 7f, the two tabs 76, 78 radially protrude from opposing sides of the bearing ring 92. A center aperture 94 permits passing of the distal portion 86 of the tightening rod 66. A top surface 96 of the bearing ring 92 may engage a shoulder 98 of the tightening rod to limit entry of the rod into the cylinder in a distal direction.

The bearing ring 92 is adapted for connection to the carriage 74. As shown in FIG. 7e, a wing 98 extends radially from a base of the bearing ring into the carriage 74, which is constructed from two pieces 74a, 74b (see FIG. 9a). The carriage may be constructed of a suitable material, such as for example, plastic or metal, and include two snap-fit pieces that enclose the wing 98. A carriage half 74a is illustrated in FIG. 7e and includes a spur 100 which is biased in a direction toward the cylinder 62 by a torsion spring 102. The spur 100 is operated by a handle 103 (see FIG. 9a) to permit threading of the band 28 in a proximal direction through a channel 104 in the carriage 74. Teeth on the spur 100 prohibit return movement of the band in the distal direction.

Figure 9A:
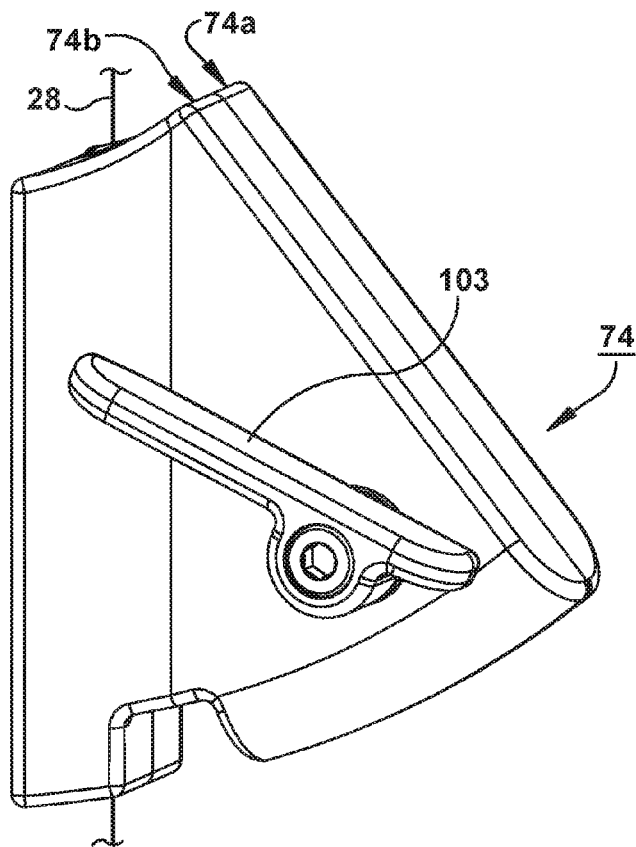
FIG. 9a is an enlarged perspective view of the carriage of FIG. 8.
Figure 9B:
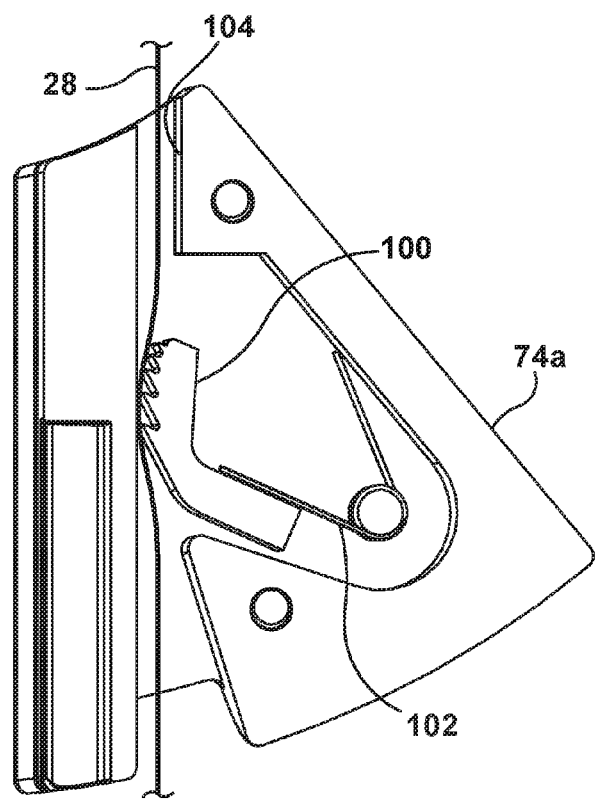

FIG. 8 shows the band 28 inserted through the carriage 74 and properly positioned for use of the tensioning instrument. The carriage is in a non-tightened position in FIG. 8. Front perspective and cross-sectional views of the carriage 74 are shown in FIGS. 9a and 9b, respectively, with the band 28 in an inserted position. As shown in FIG. 9b, teeth on the spur 100 press the band 28 against the wall of the channel 104.

As previously discussed, a surgeon may secure the housing 10 in place relative to the targeted vertebra by manipulation of the tightening rod 66. Referring now to FIG. 10a, a tightening tool 110 is shown engaged with the knob 82 of the tightening rod 66. As shown, the rod 66 has been turned and axially moved in a proximal direction away from the housing 10. As such, the carriage has moved axially along the exterior of the cylinder 62, and within the range between the slot 70 distal end 70a and proximal end 70b, at the discretion of the surgeon. As the carriage moves proximally, the band 28 is tensioned in a proximal direction securing the vertebral structure relative to the implant rod. The carriage is in a tightened position in FIG. 10a.

FIG. 10b is perspective view of the tightening tool 110 of FIG. 10a. The tightening tool includes a palm handle 54 and an instrument shaft 112, which terminates at a head 114 for engaging a recess in the knob 82. As previously discussed in regard to other tools, the palm handle 54 may separate from the instrument shaft 112 so that a single handle can accommodate multiple shafts for multiple purposes during implantation.

After the band 28 is sufficiently tensioned, the surgeon may lock the set screw 36 into a desired and final position.

Figure 11C:
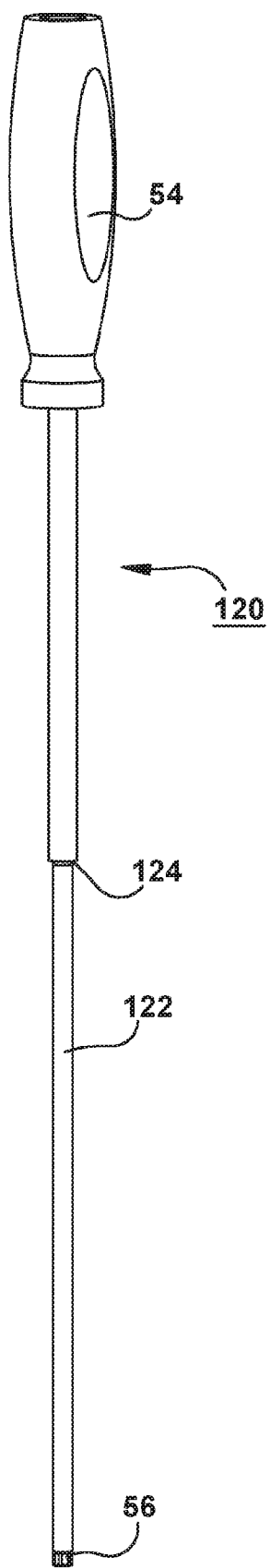

FIGS. 11a-11c detail aspects of this locking process. In FIG. 11a, a perspective view of FIG. 10a is shown with the carriage in a tightened position, the tightening tool 110 removed, and a screwdriver tool 120 inserted within the tensioning instrument 60. An enlarged cross-sectional view of the head 56 of the screwdriver tool 120 engaged with the set screw 36 is shown in FIG. 11b. In this position, the surgeon may tighten the set screw as desired by turning the tool 120.

FIG. 11c is perspective view of the screwdriver tool 120. The tool includes a palm handle 54 and an instrument shaft 122, which terminates at a head 56 for engaging the recess 42 in the set screw. As previously discussed in regard to other tools, the palm handle may separate from the instrument shaft. The exemplary shaft 122 shown includes a shoulder 124 to accommodate the internal dimensions of the cylinder 62 and tightening rod 66.

Another embodiment on the tensioning instrument will now be discussed. The tensioning instrument 160 and related parts are illustrated in FIGS. 15-23. The tensioning instrument 160 has similar features as the discussed embodiment of FIGS. 5a-11b. However, the tensioning instrument 160 includes structural differences of certain components related to tensioning. The embodiment discussed is exemplary only, and other structural difference of the same or different components can be utilized in the practice of the invention.

Figure 15:
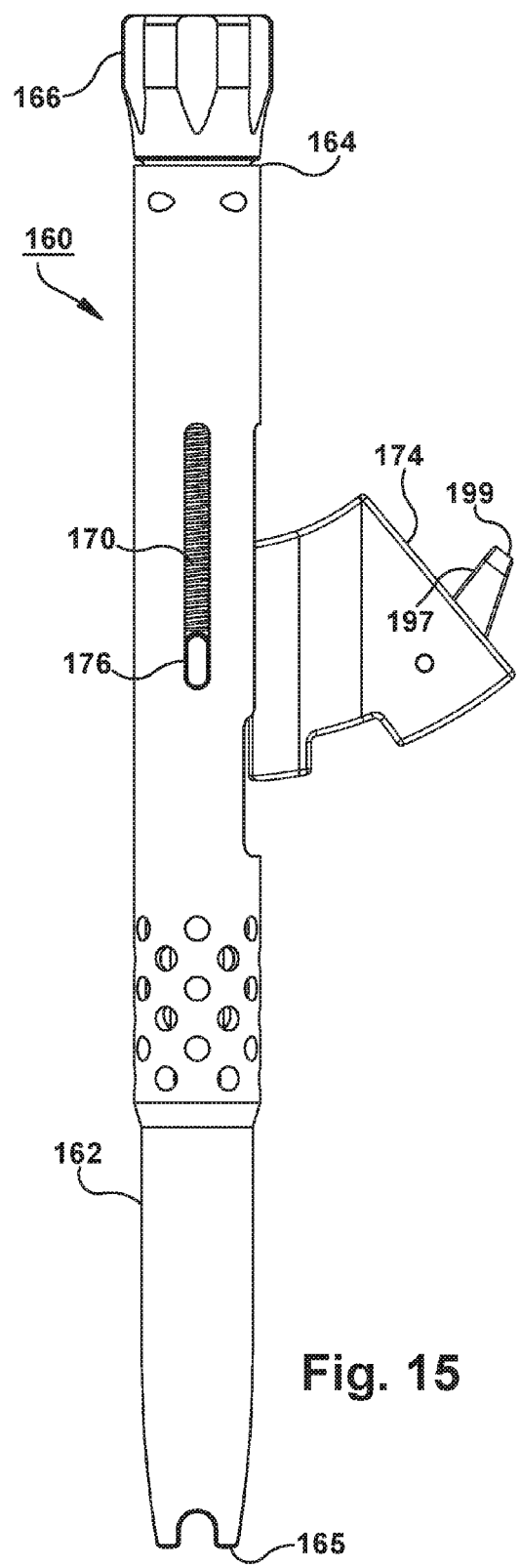
FIG. 15 is a front view of a tensioning instrument.
Figure 16:
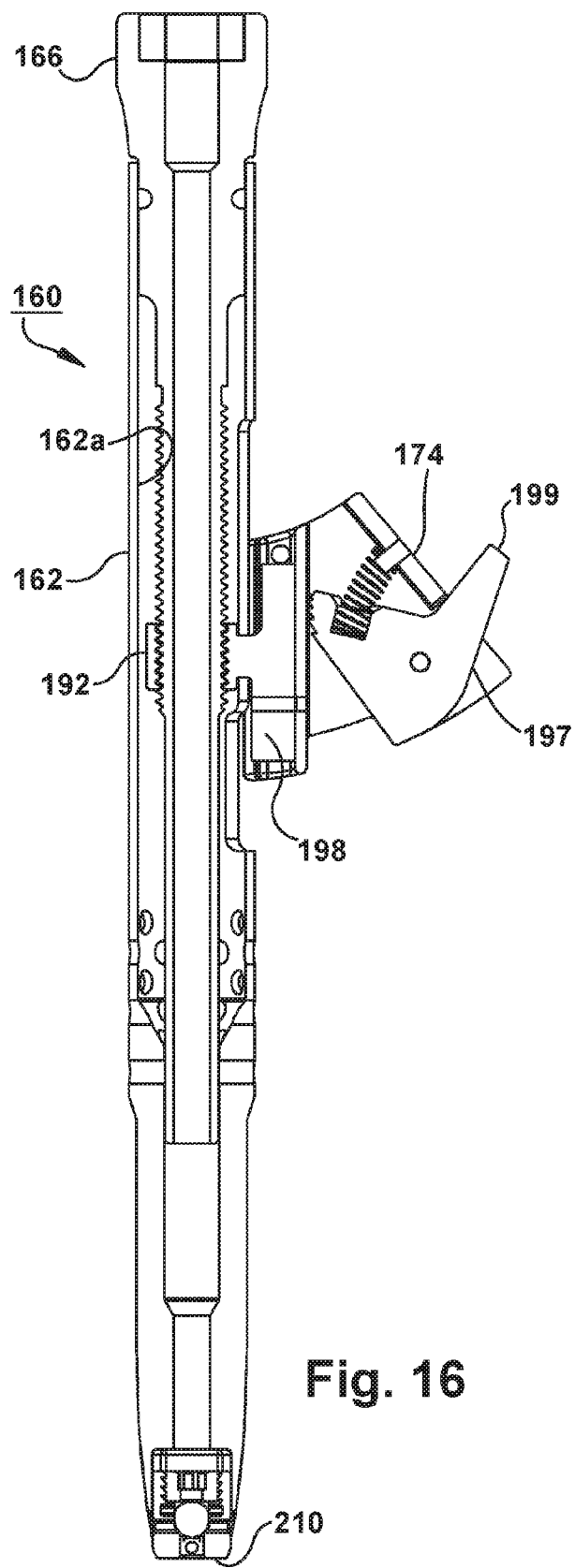
FIG. 16 is a front sectional view of the tensioning instrument of FIG. 15.
Figure 17:
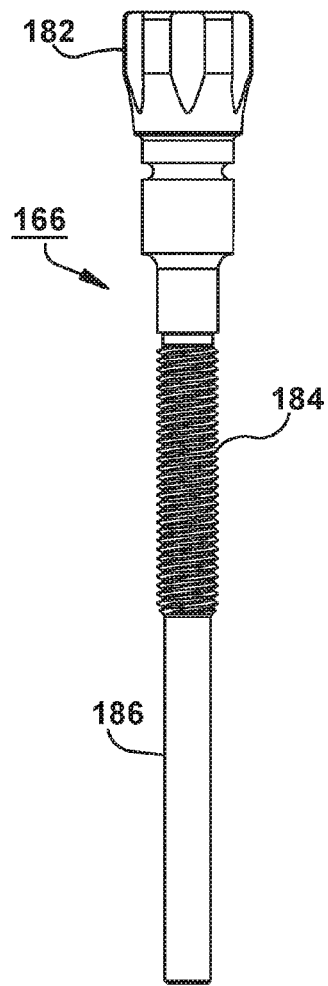
FIG. 17 is front view of a tightening rod of the tensioning instrument of FIG. 15.
Figure 18:
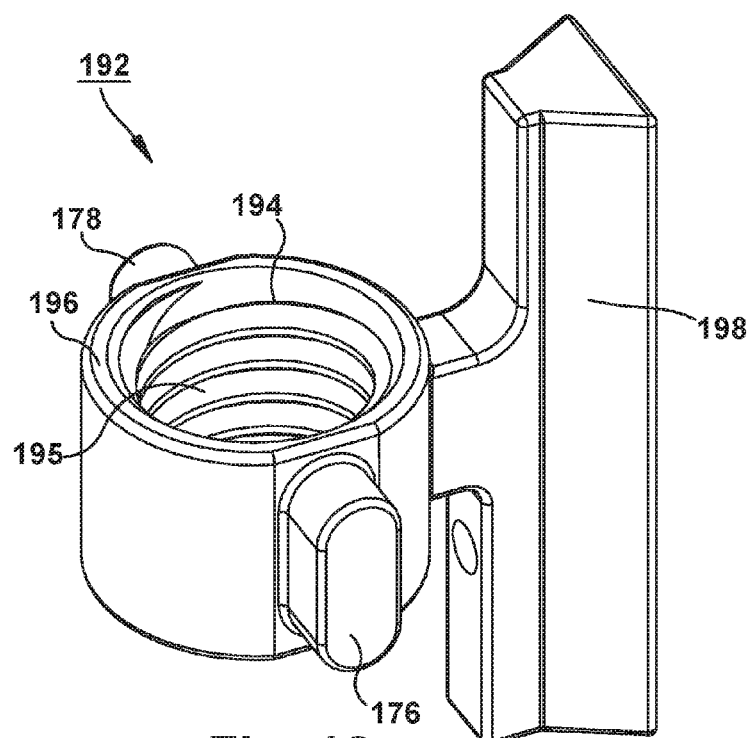
FIG. 18 is a perspective view of a bearing ring of the tensioning instrument of FIG. 15.

FIGS. 15 and 16 illustrate front and sectional views, respectively, of a tensioning instrument. The tensioning rod 166 is fixed by one or more pins and moves only axially upon rotation. In other words, the tensioning rod does not translate along the longitudinal axis of the tensioning instrument. As seen in FIGS. 16, 17 and 18, the inside of the bearing ring is threaded, and no retaining ring or set screws are included in the assembly as in other embodiments. The cross-sectional view of FIG. 21 shows detail of the tensioning rod, bearing ring and carriage assembly.

Referring specifically now to FIG. 15, a front view of a tensioning instrument 160 is illustrated. The tensioning instrument includes a hollow cylinder 162. As best shown in the sectional view of FIG. 16, the cylinder has a smooth internal surface 162 without female threads. With the internal surface being smooth, the threaded portion 184 of the tightening rod 166 does not engage the inside surface of the hollow cylinder 162. As shown in FIGS. 16-18 and 21, the tightening rod 166 engages a bearing ring 192. Specifically, a threaded surface 184 of the tightening rod engages an inside threaded surface 195 of the bearing ring 192.

The bearing ring 192 is adapted for connection to the carriage 174. As shown in FIG. 18, a wing 198 extends radially from a base of the bearing ring. The wing extends into the carriage 174 as in a previously discussed embodiment. Two tabs 176, 178 are oval in shape and ride with a slot 170 on either side of the tensioning instrument 160 as the carriage travels from a lower non-tensioned position to a higher tensioned position, as previously discussed.

The carriage advantageously "auto-locks" in operation, prohibiting disengagement of the band in the distal direction, but allowing for easy slack removal by pulling in the proximal direction.

Figure 19:
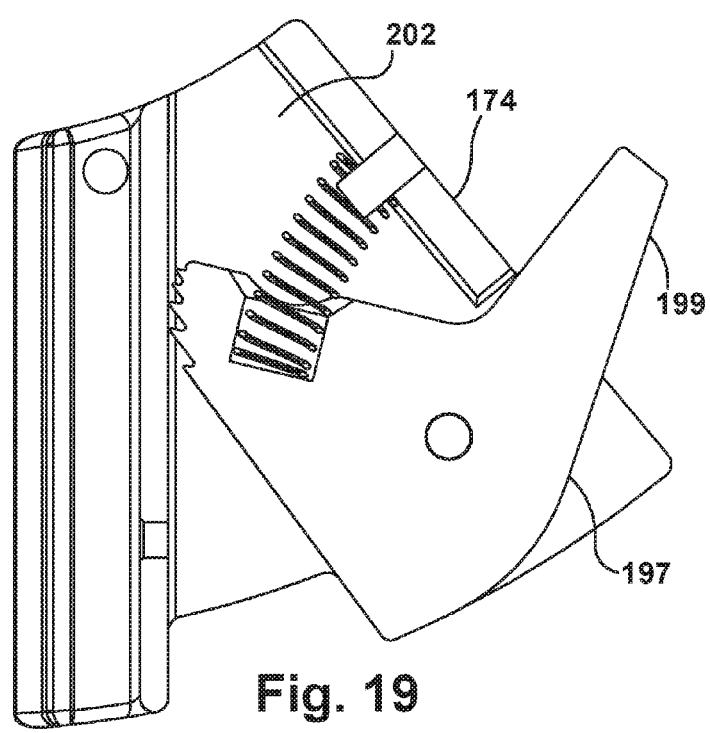
FIG. 19 is a front cross-sectional view of the carriage of FIG. 15.
Figure 22:
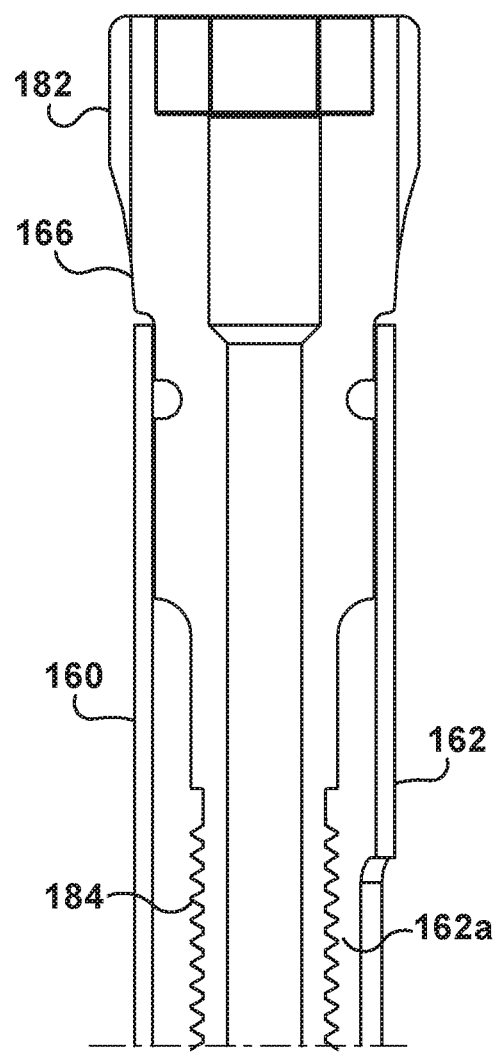
FIG. 22 is a cross-sectional view of a top portion of the tensioning instrument of FIG. 15, shown with the tightening rod installed.
Figure 23:
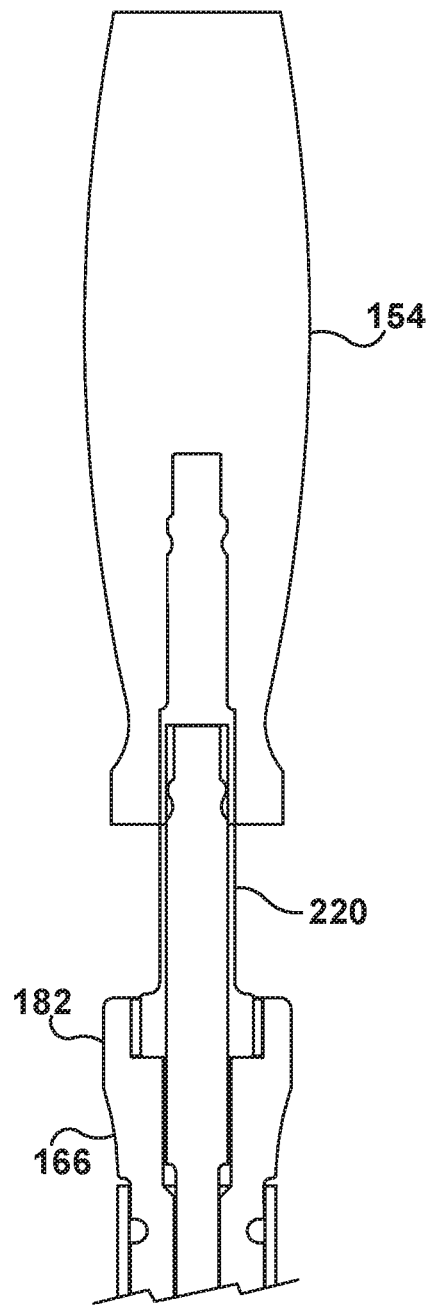
FIG. 23 is a cross-sectional view of a top portion of the tensioning instrument of FIG. 15, shown with the screwdriver tool installed.

174 illustrated in FIGS. 16 and 19 includes a lever 200 which is biased in a direction toward the cylinder 162 by a torsion spring 202. The lever 200 is operated by a handle 199 to permit threading of a tether band in a proximal direction through a channel 204 in the carriage 174. Teeth 200 on the lever 197 prohibit return movement of the band in the distal direction.

Figure 24A:
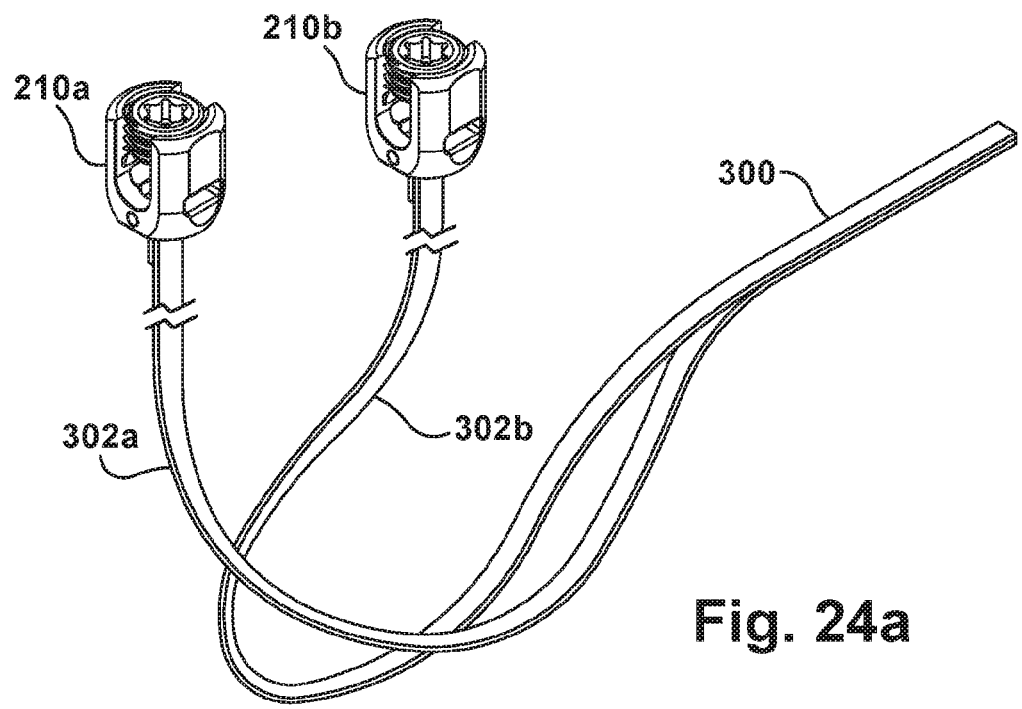
FIG. 24a is a perspective view of another embodiment of the invention, showing a dual tether band assembly.
Figure 24B:
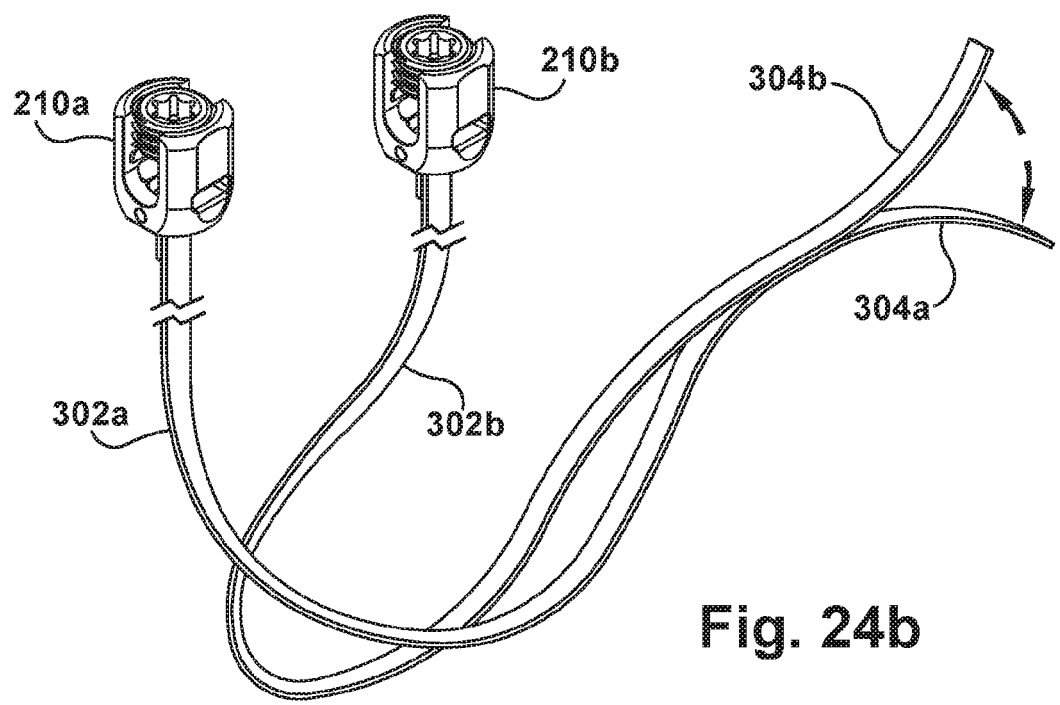
FIG. 24b is a perspective view of the assembly of FIG. 24a, shown with a part of the dual tether band split into two individual bands.

The invention can be utilized in various applications and techniques. Several other embodiments of the invention and methods of use as illustrated in FIGS. 24a-32. A dual housing assembly is illustrated in FIGS. 24a-24b. The figures illustrate two housings 210a, 210b with a dual tether band 300 fixed to the bottom of each housing. The strands are connected to the housing as by the arrangement shown in FIG. 14, with the individual strands 302a, 302b of the band connected to a pin inserted through the housing. The proximal end of the band can be split in two ends 304a, 304b after being passed through as lot on another housing, or other device. After splitting and passing, each end 304a, 304b is secured independent of the other to each housing 210a, 210b, such as for example, under a surgical rod.

Figure 25:
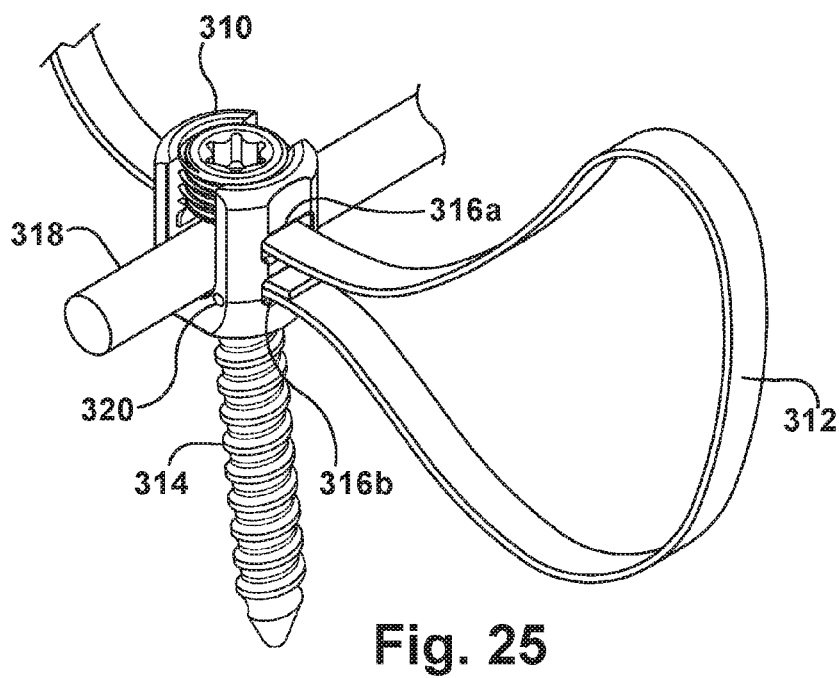
FIG. 25 is a perspective view of another embodiment of the invention, showing a tether band/pedicle screw assembly.
Figure 26:
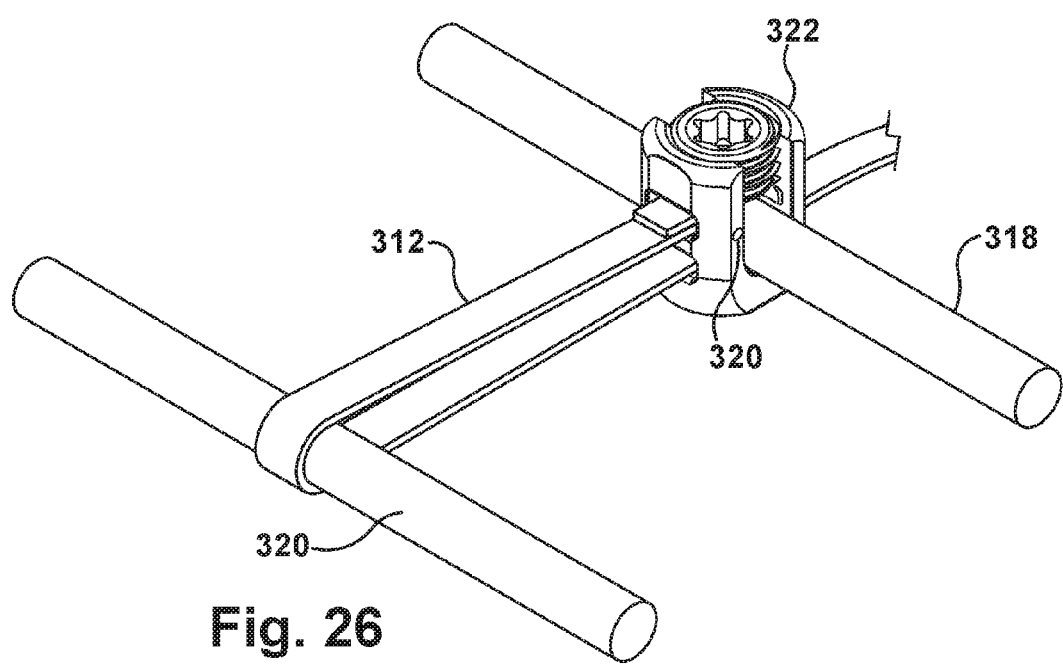
FIG. 26 is a perspective view of another embodiment of the invention, showing a tether band/cross-connector assembly.

Other embodiments of the invention can include housings having pedicle screw capability, such as for example, the housing illustrated in FIG. 25. The housing 310 includes a screw portion 314 having construction suitable for use as a pedicle screw. One or more slots allow for anchoring or passing of a tether band. As shown, a distal loop of a band 312 surrounds a mounting pin 320 and exits a lower slot 316b, and upon re-entry to the housing 310 passes through an upper slot 316a and over a surgical rod 318. This arrangement allows for additional fixation options, such as for example, to support resistance to screw pullout, e.g., in osteopenic bone. A similar arrangement is shown in FIG. 26, in which a band surrounds a second surgical rod 320. In this embodiment, the band is mounted to a pin 320 and exits out an upper slot. In this arrangement with two surgical rods 318, 320, the assembly is used as a cross connector to add bi-lateral stability in rod/implant constructs.

Figure 27A:
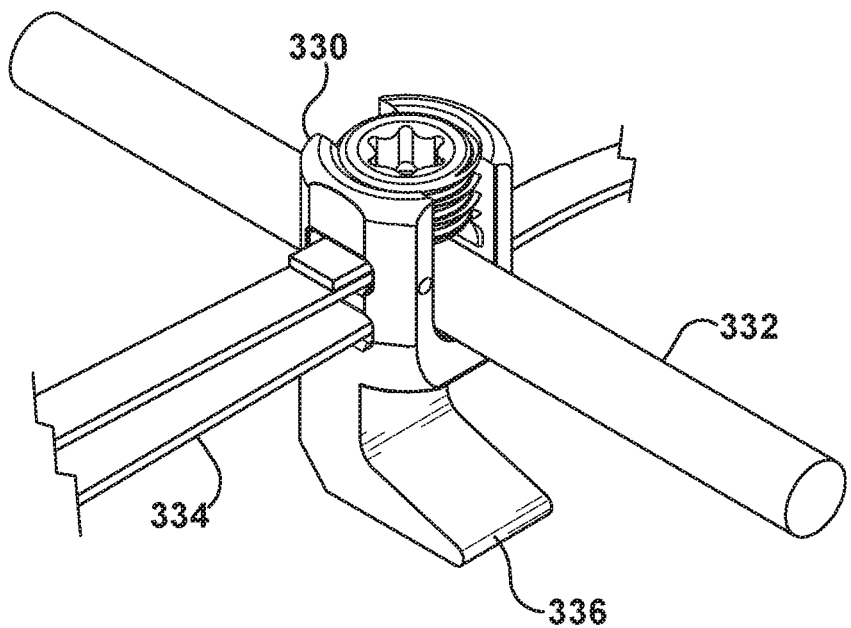
FIG. 27a is a perspective view of another embodiment of the invention, showing a tether band/hook assembly with the hook and the band in an opposite orientation.
Figure 27B:
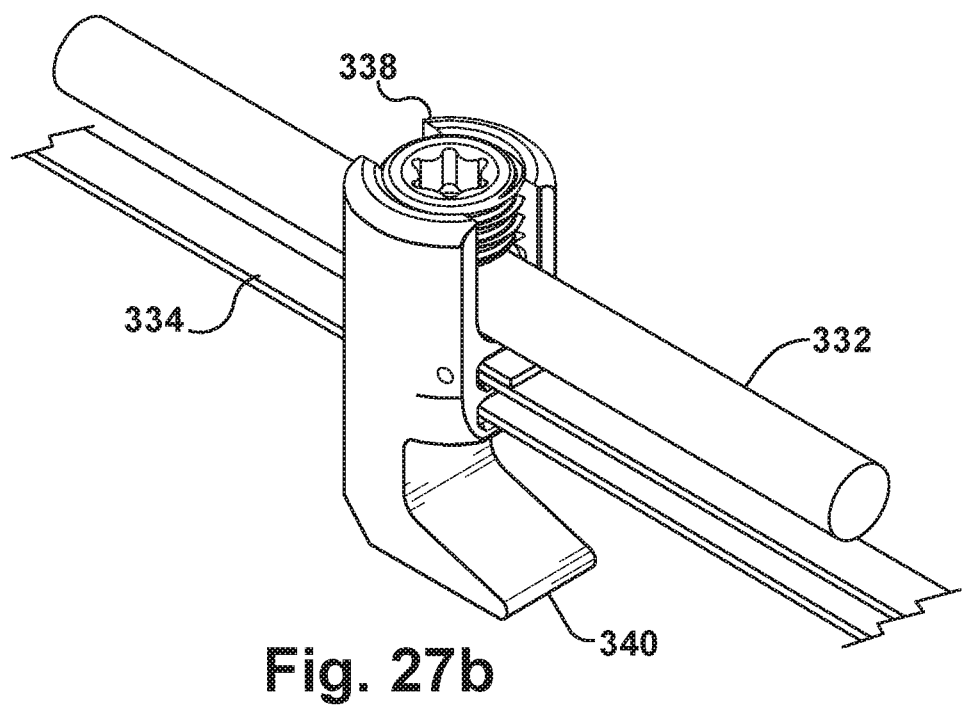
FIG. 27b is a perspective view of another embodiment of the invention, showing a tether band/hook assembly.

Other embodiments of the invention can include housings with laminar hooks used to engage bone. Specifically, the housing along the combination of hook, rods and tethers to prevent dislodging of hook, for example, to prevent proximal junctional kyphosis. FIGS. 27a and 27b illustrate housing 330, 338 with hooks 336, 340, respectively. In FIG. 27A, the rod 332 and tether 334 are positioned at opposing orientations, and with the tether above the rod. In contrast, the housing 338 of FIG. 27b positions the rod above the tether and at the same orientation, i.e., in a co-axial position. Other combinations of rod and tether positions can be practiced with this invention.

Figure 28:
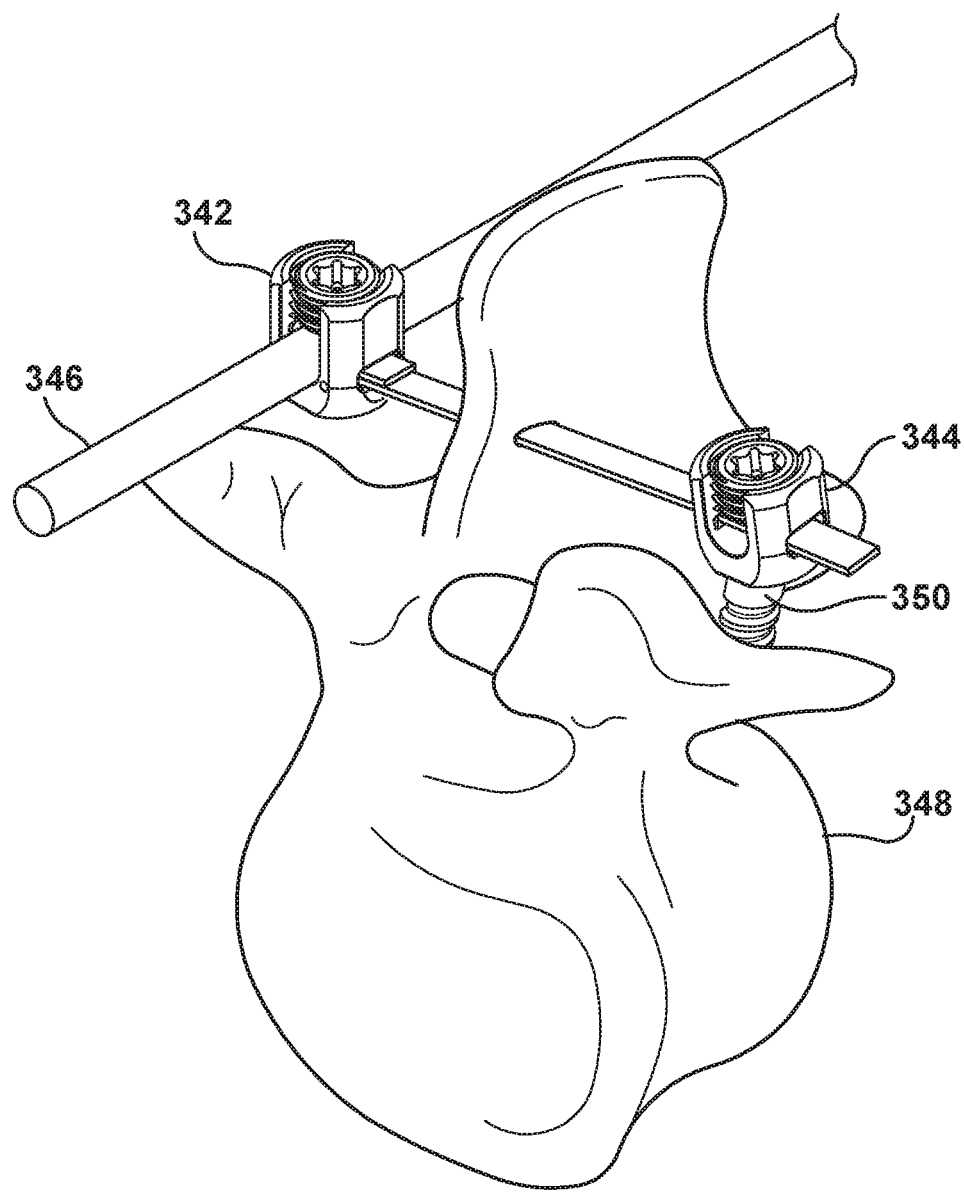
FIG. 28 is a perspective view of another embodiment of the invention, showing a two housing assembly and a transverse tether band.

Another exemplary assembly is shown in FIG. 28. As shown, a pedicle screw housing 344 is implanted into a vertebrae 348. A second housing is fixed to a rod 346 and positioned on a opposite side of the vertebrae 348 relative the pedicle screw housing 344. A tether 350 stretches from a pin mounting in the housing 342, through a surgical created slot in the vertebrae, and to the pedicle screw housing 344. The use of tether band 350 in a transverse arrangement helps derotation of vertebral body and prohibits any creep of construct.

Figure 29:
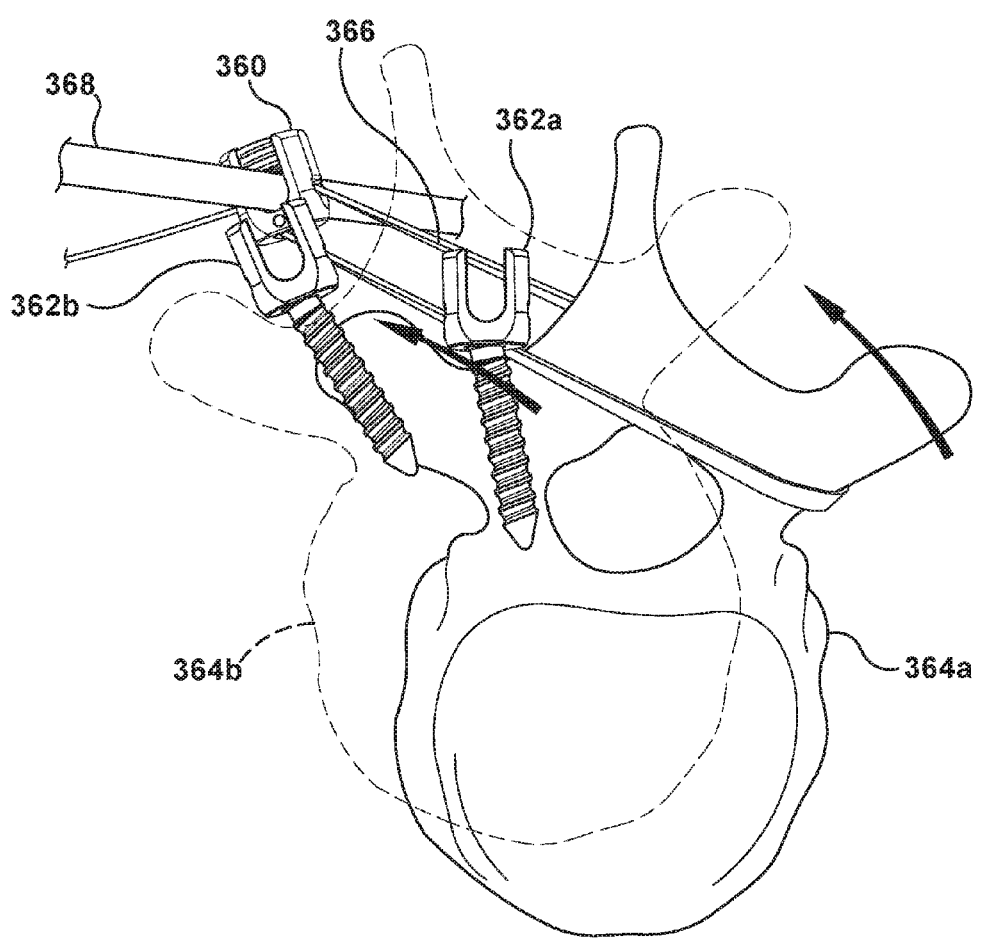
FIG. 29 is a perspective view of another embodiment of the invention, showing the installation of a tether band/pedicle screw assembly acting as a reduction device.

Multiple inventive housings and a tether band can also be advantageously used during surgery to help implant a rod. For example, FIG. 29 illustrates an exemplary use of a first housing, a pedicle screw housing, and a tether 366 in which the tether band is used to laterally translate the pedicle screw housing to the implant rod. After the first housing 360 is mounted to a rod 368, the pedicle screw housing 362a (as shown in a first position) is translated to a second position 362b by use of the tether, in effect moving the vertebrae (from a first position 364a to a second position 364b) to an position engageable with the rod 368.

Figure 30:
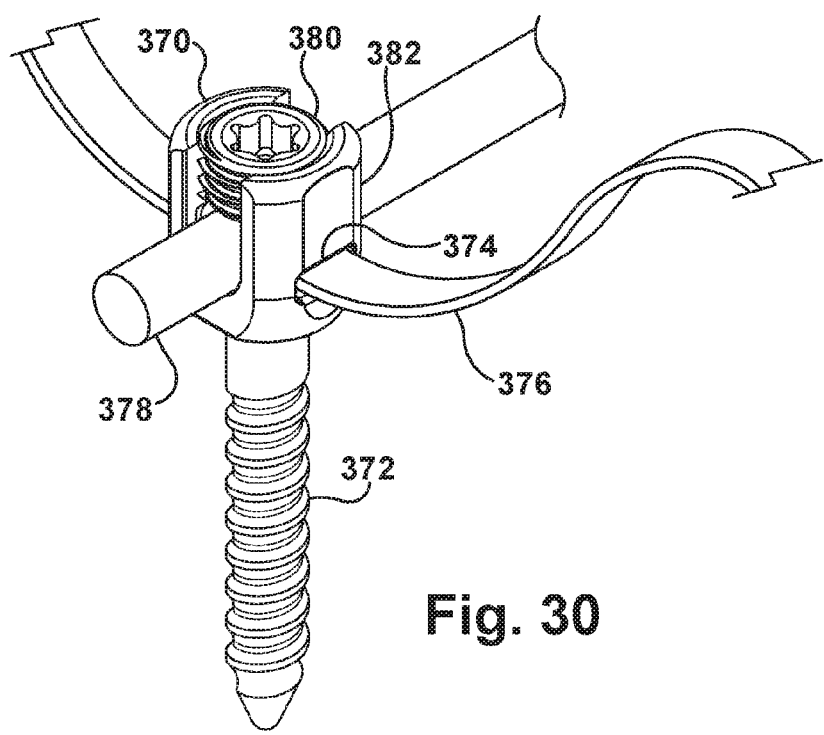
FIG. 30 is a perspective view of another embodiment of the invention, showing another tether/band/pedicle screw assembly.
Figure 31A:
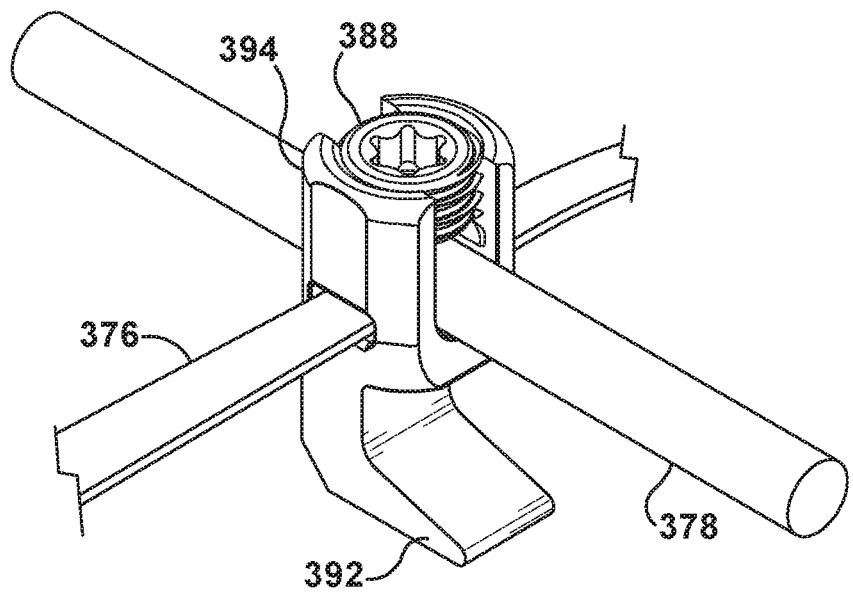
FIG. 31a is a perspective view of another embodiment of the invention, showing a tether band/rod/hook assembly.
Figure 31B:
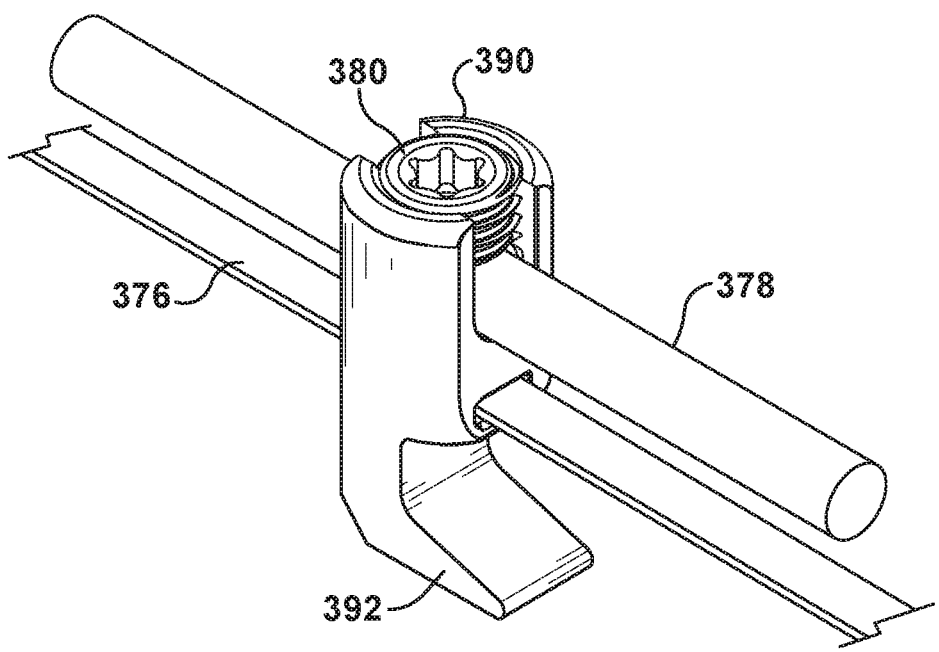
FIG. 31b is a perspective view of another embodiment of the invention, showing another tether band/rod/hook assembly.

As discussed, the inventive housing include slots suitable for passing of a tether. For example, pedicle screws with slots for tether band may be used to allow additional fixation options by accommodating passage of a tether band thru the head of the screw. As shown in FIG. 30, a pedicle screw housing 370 includes a screw portion 372, and a head 382 having a slot 374 in each arm. A tether 376 may pass above or below a surgical rod 378, and may be held in place by a set screw 380. Other examples using hooks 392 are illustrated in FIGS. 31a and 31b. These housings 394, 390 allow for additional fixation options by accommodating passage of a tether band 376 through the body of the housing transversely (as shown in FIG. 31a) or along the axis of the rod 378 (as shown in FIG. 31b). Other orientation combinations are possible in practice of invention.

Figure 32:
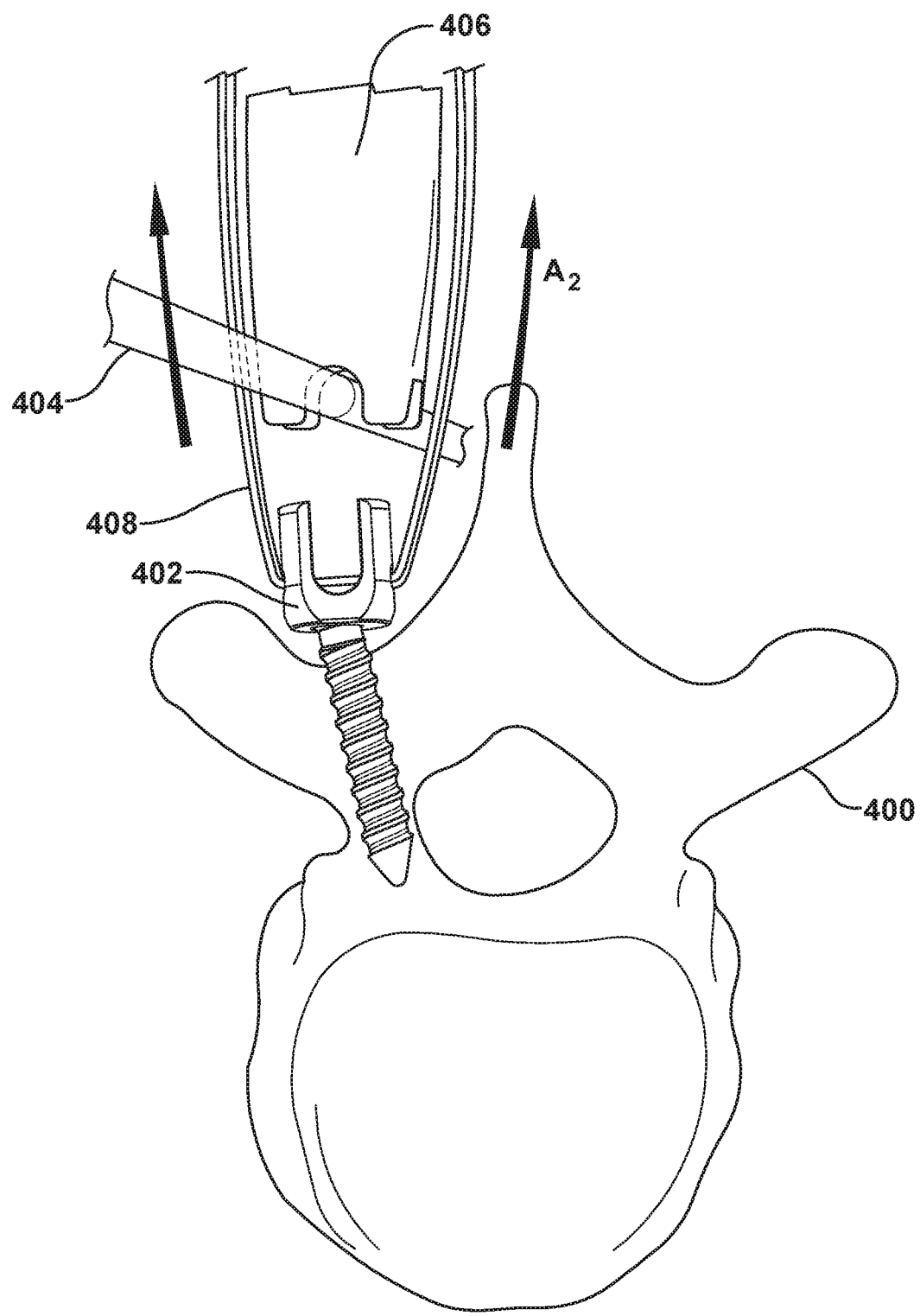
FIG. 32 is a front view of a tether band/pedicle screw assembly as used in a reduction process.

Referring now to FIG. 32, a tether band and pedicle screw housing is shown in use in a reduction process. Specifically, a tether 408 is used as a reduction device to seat a rod 404 into a pedicle screw housing 402. As shown, the housing is implanted into a vertebrae 400. By use of tensioning instrument 406, the vertebrae 400 and housing 402 is moved in a direction $A_2$ to seat the rod in a desired position.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, software, hardware, control logic, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. A clamp system comprising:
   a clamp assembly comprising
      a housing defining a longitudinal axis, a recess, a base, a distal bottom surface, and one of:
         an elongate slot aperture on the bottom surface of the base, and two opposing coaxial holes and a pin insertable therein, the coaxial holes and inserted pin positioned to bisect the elongate slot aperture;
         two elongate slot apertures, one in a side of the base near the bottom surface and one in the bottom surface;
         two elongate slot apertures positioned on opposite sides of the base near the bottom surface; and
         two elongate slot apertures positioned on opposite sides of the base near the bottom surface and a third elongate slot aperture positioned on the bottom surface
      a rod insertable through the recess into the base;
      a locking element having a tool-engaging surface, and positionable proximally within the recess in a co-axial relationship to the longitudinal axis of the housing; and
      a band sized for travel along a predetermined path defined in part by at least one slot aperture in the housing and the rod;
   a tensioning instrument comprising
      a hollow body having a proximal end and a distal end, the proximal end configured for insertion of a tool into a length of the tensioning instrument, the distal end engageable with the clamp housing in a co-axial relationship;
      a carriage for receiving and tensioning a band that is inserted through the slots of the housing, the carriage comprising at least one channel for insertion of a band, a band securing mechanism; and
      a tension tightening rod;
   a locking tool engageable with the locking element
   wherein the tensioning instrument defines at least one travel slot which permits movement of the carriage between a band non-tightened position and a band tightened position when the tightening rod is manipulated; and,
   wherein, the band is passable along a path from beneath the rod and through at least one of the at least one slot; and,
   wherein the band is secured to the clamp by the application of tension with the tensioning instrument and manipulation of the locking tool to press the locking element against the rod to pinch the band and secure the locking element into engagement with the clamp housing.

2. A clamp system according to claim 1, wherein an axial position of the carriage is controllable by user manipulation of the tension tightening rod.

3. A clamp system according to claim 1 comprising a tensioning tool sized for manipulation of the tension tightening rod when the housing, locking element, tensioning instrument, and tensioning rod are positioned along a common longitudinal axis.

4. A clamp system according to claim 1, the recess in the clamp housing defining two opposing arms shaped to retain the rod, wherein the arms form opposing U shaped concavities that retain the rod, wherein the distal end of the tensioning instrument is slideable over the outside surfaces of the two opposing arms.

5. A clamp system according to claim 1, wherein the rod is sized to extend laterally through the arms beyond the sides of the base.

6. A clamp system according to claim 1, wherein the locking element is selected from a set screw, a blocking nut and a blocker.

7. A clamp system according to claim 1, wherein a mating engagement surface of the recess is threaded.

8. A clamp system according to claim 1, wherein the clamp housing is generally cylindrical in shape.

9. A clamp system according to claim 1, wherein a first end of the band is fixed to the clamp housing.

10. A clamp system according to claim 9, the clamp housing comprising two elongate slot apertures arranged in a parallel orientation to one another on one of a side and the base of the clamp housing through which the first end of the band is passed and fixed.

11. A clamp system according to claim 1, wherein the tensioning instrument comprises a feature for engagement with the clamp housing to provide a counter force for applying tension to the band.

12. A clamp system according to claim 1, wherein the tensioning instrument further comprises a feature for engagement with the rod to maintain its position in the distal portion of the housing prior to insertion of the locking element.

13. A clamp system according to claim 1, wherein the instrument band securing mechanism comprises a toothed engagement feature that "auto-locks" in operation, prohibiting loosening of the band and travel in the distal direction as it is pulled into tension, but allowing for easy slack removal by pulling in the proximal direction.

14. A band clamp system comprising:
a clamp assembly comprising:
    a unitary clamp housing comprising
        a recess extending along an axis through a base and toward a distal bottom surface, the recess shaped for receiving a distally placed rod, and having an internal mating surface for engagement with a locking element positionable proximally within the recess,
        at least one aperture through one of a side of the clamp housing and the bottom surface of the clamp housing base, wherein the at least one aperture is an elongate slot,
    a band that is passable through the at least one elongate slot aperture of the clamp housing;
    a rod insertable through the recess into the base; and
    a locking element positionable in a co-axial relationship within the recess and having an external circumferential surface for engagement with the internal mating surface of the clamp housing;
a tensioning instrument comprising
    a hollow body having a proximal end and a distal end, the proximal end configured for insertion of a tool into a length of the tensioning instrument, the distal end engageable with the clamp housing in a co-axial relationship;
        a carriage for receiving and tensioning a band that is inserted through the at least one of the at least one elongate slot aperture of the housing, the carriage comprising at least one channel for insertion of a band, a band securing mechanism; and
        a tension tightening rod;
        a locking tool engageable with the locking element
    wherein the tensioning instrument defines at least one travel slot which permits movement of the carriage between a band non-tightened position and a band tightened position when the tightening rod is manipulated; and,
    wherein, the band is passable along a path from beneath the rod and through at least one of the at least one elongate slot aperture; and,
    wherein the band is secured to the clamp by the application of tension with the tensioning instrument and manipulation of the locking tool to press the locking element against the rod to pinch the band and secure the locking element into engagement with the clamp housing.

15. A band clamp system according to claim 14, wherein a first end of the band is fixed to the unitary clamp housing.

16. A band clamp system according to claim 15, the clamp housing comprising two elongate slot apertures arranged in a parallel orientation to one another on one of a side and the base of the clamp housing through which the first end of the band is passed and fixed.

17. A band clamp system according to claim 14, wherein the rod is sized to extend laterally through the arms beyond the sides of the base.

18. A band clamp system according to claim 14, wherein the clamp housing is generally cylindrical in shape.

19. A band clamp system according to claim 14, the recess in the clamp housing defining two opposing arms shaped to retain the rod, wherein the arms form opposing U shaped concavities that retain the rod, wherein the distal end of the tensioning instrument is slideable over the outside surfaces of the two opposing arms, and wherein a mating engagement surface of the recess is threaded.

20. A band clamp system according to claim 14, wherein the locking element is selected from a set screw, a blocking nut and a blocker.

21. A band clamp system according to claim 14, wherein the tensioning instrument comprises a feature for engagement with the clamp housing to provide a counter force for applying tension to the band.

22. A band clamp system according to claim 14, wherein the tensioning instrument further comprises a feature for engagement with the rod to maintain its position in the distal portion of the housing prior to insertion of the locking element.

23. A band clamp system according to claim 14, wherein the tensioning instrument band securing mechanism comprises a toothed engagement feature that "auto-locks" in operation, prohibiting loosening of the band and travel in the distal direction as it is pulled into tension, but allowing for easy slack removal by pulling in the proximal direction.

* * * * *

UNITED STATES PATENT AND TRADEMARK OFFICE
CERTIFICATE OF CORRECTION

Page 1 of 1

PATENT NO. : 9,770,268 B2
APPLICATION NO. : 15/058582
DATED : September 26, 2017
INVENTOR(S) : Michael Albert et al.

It is certified that error appears in the above-identified patent and that said Letters Patent is hereby corrected as shown below:

On the Title Page

Column 1, Item (60) should read:
RELATED US APPLICATION DATA
Division of application No. 14/746,226, filed on Jun. 22, 2015, which is a division of application No. 13/618,724, filed on Sep. 14, 2012, now Pat. No. 9,173,685.

In the Specification

Column 1, Line 4 should read:
CROSS-REFERENCE TO RELATED APPLICATION
This non-provisional application is a division of U.S. Non-Provisional patent application Ser. No. 14/746,226, filed Jun. 22, 2015, now U.S. Pat. No. 9,770,267, issued on Sep. 26, 2017, which is in turn a division of U.S. Non-Provisional patent application Ser. No. 13/618,724, filed Sep. 14, 2012, now U.S. Pat. No. 9,173,685, issued on Nov. 3, 2015, each of which claims the benefit of U.S. Provisional Patent Application Ser. No. 61/534,453, entitled TETHER CLAMP AND IMPLANTATION SYSTEM, filed Sep. 14, 2011, and U.S. Provisional Patent Application Ser. No. 61/595,296, entitled TETHER CLAMP AND IMPLANTATION SYSTEM, filed Feb. 6, 2012, the entire disclosure of each of which applications is incorporated herein by reference, to the extent that said disclosures do not conflict with the present application.

Signed and Sealed this
Fourteenth Day of July, 2020

Andrei Iancu
*Director of the United States Patent and Trademark Office*